US007801683B2

(12) United States Patent
Vandezande

(10) Patent No.: US 7,801,683 B2
(45) Date of Patent: Sep. 21, 2010

(54) HIERARCHICAL OPTIMIZATION FOR PROCEDURAL EFFECTIVENESS IN DIAGNOSING MUTATIONS THAT RELATE TO DISEASE

(76) Inventor: Kirk Edward Vandezande, 106-365 Dundas St. East, Toronto (CA) M5A 4R9

( * ) Notice: Subject to any disclaimer, the term of this patent is extended or adjusted under 35 U.S.C. 154(b) by 756 days.

(21) Appl. No.: 10/629,380

(22) Filed: Jul. 29, 2003

(65) Prior Publication Data
US 2004/0091916 A1    May 13, 2004

Related U.S. Application Data

(60) Provisional application No. 60/398,780, filed on Jul. 29, 2002.

(51) Int. Cl.
*G01N 33/48* (2006.01)
*C12Q 1/68* (2006.01)
(52) U.S. Cl. .................................. 702/19; 702/20; 435/6
(58) Field of Classification Search ........................ None
See application file for complete search history.

(56) References Cited

U.S. PATENT DOCUMENTS

| | | | |
|---|---|---|---|
| 5,545,527 | A | 8/1996 | Stevens et al. |
| 5,550,020 | A | 8/1996 | Gallie et al. |
| 6,063,567 | A | 5/2000 | Gallie et al. |
| 6,270,963 | B1 | 8/2001 | Stevens et al. |
| 6,403,303 | B1 | 6/2002 | Shipman et al. |

OTHER PUBLICATIONS

United States Patent and Trademark Office, "Interim Guidelines for Examination of Patent Applications for Patent Subject Matter Eligibility." Retrieved and printed from the US PTO website at http://www.uspto.gov/web/offices/com/sol/og/2005/week47/og200547.htm on Jul. 24, 2006.*
Bapat et al., Gut, vol. 44, pp. 698-703, 1999.*
Antonarakis, Stylianos E. And the Nomenclature Working Group (1998). Recommendations for a nomenclature system for human gene mutations. Human Mutation 11(1):1-3. Hoboken, NJ: Wiley-Liss, Inc.
Benedict WF, Murphree AL, Banerjee A, Spina CA, Sparkes MC, Sparkes RS. Patient with 13 chromosome deletion: evidence that the retinoblastoma gene is a recessive cancer gene. Science 219(4587):973-5 (Feb. 25, 1983).
Blanquet V, Turleau C, Gross-Morand MS, Sénamaud-Beaufort C, Doz F, Besmond C. Spectrum of germline mutations in the RB1 gene: a study of 232 patients withhereditary and non hereditary retinoblastoma. Hum.Mol.Genet. 4:383-388 (1995).
Carter MS, Doskow J, Morris P, Li S, Nhim RP, Sandstedt S, Wilkinson MF. A regulatory mechanism that detects premature nonsense codons in T-cell receptor transcripts in vivo is reversed by protein synthesis inhibitors in vitro. J Biol Chem 270:28995-9003 (1995).

Cystic Fibrosis Genotype-Phenotype Consortium. Correlation between Genotype and Phenotype in Patients with Cystic Fibrosis. N Eng J Med 329(18):1308-1313 (1993).
Den Dunnen JT, Antonarakis E. Nomenclature for the description of human sequence variations Hum Genet 109:121-124 (2001).
Den Dunnen JT, Grootscholten PM, Bakker E, Blonden LA, Ginjaar HB, Wapenaar MC, van Paassen HM, van Broeckhoven C, Pearson PL, van Ommeo GJ. Topography of the Duchenne muscular dystrophy (DMD) gene: FIGE and cDNA analysis of 194 cases reveals 115 deletions and 13 duplications. Am J Hum Genet 45(6):835-47 (Dec. 1989).
Diciommo D, Gallie BL, Bremner R. Retinoblastoma: the disease, gene and protein provide critical leads to understand cancer. Semin Cancer Biol 10:255-69 (2000).
Dunn JM, Phillips RA, Zhu X, Becker AJ, Gallie BL. Mutations in the RB1 gene and their effects on transcription. Mol. Cell. Biol. 9:4594-4602 (1989).
Gad S, Aurias A, Puget N, Mairal A, Schurra C, Montagna M, Pages S, Caux V, Mazoyer S, BensimonA, Stoppa-Lyonnet D (2001) Color bar coding the BRCA1 gene on combed DNA: a useful strategy for detecting large gene rearrangements.Genes Chromosomes Cancer 31(1):75-84 (May 2001).
Hegde MR, Chong B, Fawkner MJ, Leary J, Shelling AN, Culling B, Winship I, Love DR. Hierarchical mutation screening protocol for the BRCA1 gene. Human Mutation 16(5):422-30 (Nov 2000).
Hentze MW, Kulozik AE. A perfect message: RNA surveillance and nonsense-mediated decay. Cell 96:307-10 (1999).
Janson M, Nordenskjold M. A constitutional mutation within the retinoblastoma gene detected by PFGE. Clin Genet 45:5-10 (1994).
Klutz M, Brockmann D, Lohmann DR. A Parent-of-Origin Effect in Two Families with Retinoblastoma is Associated with a Distinct Splice Mutation in the RB1 Gene. Am J Hum Genet 71:174-9 (2002).
Lee Jo, Russo AA, Pavletich NP. Structure of the retinoblastoma tumour-suppressor pocket domain bound to a peptide from HPV E7. Nature 391(6670):859-65 (1998).
Lohmann DR, Horsthemke B, Gillessen KG, Stefani FH, Hofler H. Detection of small RB1 gene deletions in retinoblastoma by multiplex PCR and high-resolution gel electrophoresis. Hum Genet 89:49-53 (1992).
Lohmann DR, Brandt B, Höpping W, Passarge E, Horsthemke B. Distinct RB1 gene mutations with low penetrance in hereditary retinoblastoma. Hum.Genet. 94:349-354 (1994).

(Continued)

*Primary Examiner*—Shubo (Joe) Zhou
(74) *Attorney, Agent, or Firm*—Norris McLaughlin & Marcus, PA; Christa Hildebrand

(57) ABSTRACT

A method for determining the optimal test order for diagnosing mutations that relate to a disease. The method includes receiving data, creating a database, receiving new data, applying at least one decision tree algorithm to score each possible test order, and generating a recommendation. The method may also determine the projected costs and the projected times to perform each test in the optimal test order. A computer readable medium for determining an optimal test order for diagnosing mutations that relate to a disease. A computer system for determining an optimal test order for diagnosing mutations that relate to a disease. The system includes a computing environment, an input device, an output device, and a plurality of decision tree algorithms. The system may also determine the projected costs and the projected times to perform each test in the optimal test order.

10 Claims, 6 Drawing Sheets

OTHER PUBLICATIONS

Lohmann DR. RB1 gene mutations in retinoblastoma. Hum Mutat 14:283-288 (1999).

McFall RC, Sery TW, Makadon M. Characterization of a new continuous cell line derived from a human retinoblastoma. Cancer Res 37:1003-1010 (1977).

Noorani HZ, Khan HN, Gallie BL, Detsky AS. Cost comparison of molecular versus conventional screening of relatives at risk for retinoblastoma. Am J Hum Genet 59:301-7 (1996).

Otterson GA, Chen W, Coon AB, Khleif SN, Kaye FJ. Incomplete penetrance of familial retinoblastoma linked to germ-line mutations that result in partial loss of RB function. Proc Natl Acad Sci USA 94:12036-40 (1997).

Schmutte C, Jones PA. Involvement of DNA methylation in human carcinogenesis. Biol Chem 379:377-88 (1998).

Sippel KC, Fraioli RE, Smith GD, Schalkoff ME, Sutherland J, Gallie BL, Dryja TP. Frequency of somatic and germ-line mosaicism in retinoblastoma: implications for genetic counseling. Am J Hum Genet 62:610-9 (1998).

Whitaker LL, Su H, Baskaran R, Knudsen ES, Wang JY. Growth suppression by an E2F-binding-defective retinoblastoma protein (RB): contribution from the RB C pocket. Mol Cell Biol 18:4032-42 (1998).

Zeschnigk M, Lohmann DR, Horsthemke B. A PCR test for the detection of hypermethylated alleles at the retinoblastoma locus [letter]. J Med Genet 36:793-4 (1999).

Vandezande, K. Hierarchical Optimization for Procedural Effectiveness; Improves Health Care for Families with Retinoblastoma. Poster presented at the American Society of Human Genetics conference (Oct. 2001).

* cited by examiner

HIERARCHICAL OPTIMIZATION FOR PROCEDURAL EFFECTIVENESS IN DIAGNOSING MUTATIONS THAT RELATE TO DISEASE

FIELD OF INVENTION

This invention relates to computer readable mediums, systems and methods for determining an optimal test order for diagnosing mutations that relate to a disease.

BACKGROUND

For certain diseases linked to autosomal dominant inheritance of genetic mutations, doctors are now able to improve medical treatment for affected people, even before clinical presentation of symptoms, due to molecular diagnosis of the heritable mutation. Some diseases that result from such heritable mutations are hereditary breast and ovarian cancer, hereditary hemorrhagic telangiectasia, cystic fibrosis, colorectal cancer and retinoblastoma.

For example, molecular diagnosis requires a comparison of patient DNA to "wild type" DNA accepted by a consensus of experts as normal. Some general classes of mutations that cause disease include deletion of all or part of a critical gene, insertions and duplications of isolated portions of DNA, and hypermethylation of gene promoter regions. In some diseases, certain genetic mutations are found to recur in the DNA of many patients, the same type of mutations at the same locations in DNA, across many individuals.

For example, in both Duchenne Muscular Dystrophy and Becker Muscular Dystrophy, mutations cluster in two recombination "hot spots". (Den Dunnen et al 1989). Similarly, the most common genetic defect that causes cystic fibrosis ($\Delta$F508) accounts for about 30-80% of mutant alleles depending on the ethnic group [CF Genotype-Phenotype Consortium1993]

More typically, however, heritable diseases are linked to mutations that do not recur with great frequency across affected families. Before any beneficial change in treatment can be offered to families affected by such a disease, first it is necessary to search the DNA for the mutation(s) that cause disease. Once the familial mutation is identified, all individuals at risk can be tested to see if they carry the mutation and beneficial changes can often be made to the surveillance or treatment of affected individuals.

The prior art in searching for genetic mutations relies first on PCR amplification and sequencing of DNA from genes linked to particular diseases. For some diseases, it is known to be cost-effective to use other preliminary screening techniques to detect the existence of a mutation and to restrict the search for sequencing errors to a smaller region of DNA. Examples of such supplementary techniques include Quantitative Multiplex PCR (QMPCR), Single Stranded Conformational Polymorphism (SSCP) analysis, and heteroduplex analysis.

Because many genetic diseases are linked to a multiplicity of genetic mutations, if molecular diagnosis is to achieve high levels of sensitivity, the analysis must involve multiple medical diagnostic assays. Although the prior art recognizes the value of multiple hierarchical assays, there is no discussion in the relevant literature to explain how one should order multiple medical diagnostic assays to achieve the shortest possible turnaround time, the lowest possible test costs, or both.

Cost effective health care requires that a molecular test methodology be shown to be sensitive, accurate and economically feasible before it becomes routine clinical care. Therefore, it is of significant economic value to health care providers that molecular test strategies are designed to provide the highest sensitivity to mutations, yet at the lowest possible cost and in the least possible time. The current invention makes such design capacity available to knowledgeable users.

SUMMARY

This invention provides a computer readable medium having computer-executable instructions that when executed by a computer cause the computer to perform a method for determining an optimal test order for diagnosing mutations that relate to a disease, the method comprising the steps of receiving data indicative of a historical frequency distribution of mutations that relate to the disease and the assays required to diagnose the disease, creating a history database, the database comprising a sequence of records based on the data, receiving new data indicative of the historical frequency distribution of mutations that relate to the disease and the assays required to diagnose the disease, applying at least one decision tree algorithm, wherein the at least one decision tree algorithm scores at least a portion of the new data and generating a recommendation if the score satisfies a threshold.

In one embodiment, applying at least one decision tree algorithm comprises the steps of accessing a set of records within the history database generating at least two strategies from the accessed records, comparing the at least two strategies against each other; and calculating the projected cost for the at least one strategy identified by the comparing step. In another embodiment the threshold is calculated from a preselected minimum number of records within the history database.

The invention further relates to a system for determining an optimal test order for diagnosing mutations that relate to a disease, comprising a computing environment; an input device, connected to the computing environment for receiving information; an output device, connected to the computing environment, for presenting information; and at least one decision tree algorithm selectively executed based on at least a portion of the new data, wherein the at least one of the decision tree algorithms scores at least a portion of the new data and determines the optimal test order associated with the at least one decision tree algorithm if the score satisfies a threshold, wherein the optimal test order is presented via the output device.

In one embodiment the at least one decision tree algorithm further determines a projected cost for each test associated with the optimal test order if the score satisfies a threshold, wherein the projected cost is presented via the output device. In another embodiment the received information comprises the historical frequency distribution of mutations that relate to the disease and the assays required to diagnose the disease. In yet another embodiment the at least one decision tree algorithm is specific to hereditary diseases selected from the group consisting of breast cancer, colorectal cancer, lung cancer, prostate cancer, retinoblastoma, and hereditary hemorrhagic telangiectasia. In another embodiment the decision tree consists of at least two strategies. In yet another embodiment the at least two strategies are ranked by projected cost and in yet another embodiment the at least two strategies comprise at least two assays. In one embodiment, the at least two strategies are ranked based on minimum projected cost to perform the at least two medical diagnostic assays.

The invention also relates to a method of determining the optimal test order for diagnosing mutations that relate to a disease, comprising the steps of receiving data indicative of a historical frequency distribution of mutations that relate to the disease and the assays required to diagnose the disease; creating a history database, the database comprising a sequence of records based on the data; receiving new data indicative of the historical frequency distribution of mutations that relate to the disease and the assays required to diagnosis the disease; applying at least one decision tree algorithm, wherein the at least one decision tree algorithm scores at least a portion of the new data; and generating a recommendation if the score satisfies a threshold. In one embodiment, applying at least one decision tree algorithm comprises the steps of accessing a set of records within the history database; generating at least two strategies from the accessed records; comparing the at least two strategies against each other; and calculating the projected cost for the at least one strategy identified by the comparing step. In yet another embodiment, the projected cost is calculated from a preselected minimum number of records within the history database.

This invention provides a computer-readable medium having computer-executable instructions that when executed by a computer cause the computer to perform a method for determining an optimal test order for diagnosing mutations in DNA that relate to a disease, the method comprising the steps of receiving through an input device data indicative of the historical frequency distribution of mutations in DNA that relate to a disease and the assays required to render a diagnosis for the disease, creating a history database, the database comprising a sequence of records based on the data, receiving, through an input device, new data indicative of the historical frequency distribution of mutations in DNA that relate to a disease and the assays required to render a diagnosis for the disease, applying a match pattern to the history database, generating a recommendation if a frequency value of matched records located by applying the match pattern satisfies a match threshold and communicating the recommendation through an output device. In one embodiment, applying a match pattern comprises accessing a set of records within the history database by use of a time window, the time window comprising a range of pre-selected dates, comparing the match pattern to each of the accessed records; and calculating the frequency value from the matched records identified by the comparing step. In another embodiment, the match threshold is representative of a pre-selected minimum number of records corresponding to the match pattern.

The present invention further relates to a system for determining an optimal test order for diagnosing mutations in DNA that relate to a disease, comprising a computing environment; an input device, connected to the computing environment for receiving information; an output device, connected to the computing environment, for presenting information; and a plurality of decision tree algorithms selectively executed based on at least a portion of the received information, wherein any one of the decision tree algorithms scores at least a portion of the received information and determines the optimal test order associated with the any one decision tree algorithm if the score reaches or passes a threshold, wherein the optimal test order is presented via the output device. In one embodiment, the any one of the decision tree algorithms further determines the projected costs for each test associated with the optimal test order if the score reaches or passes a threshold, wherein the projected costs are presented via the output device. In another embodiment, the any one of the decision tree algorithms further determines the projected times for each test associated with the optimal test order if the score reaches or passes a threshold, wherein the projected times are presented via the output device. In yet another embodiment, the any one of the decision tree algorithms further determines the path associated with the optimal test order if the score reaches or passes a threshold, wherein the path is presented via the output device. In one embodiment, the threshold is modifiable by one or more sensitivity factors. In one embodiment, the path consists of at least two strategies. In another embodiment, the at least two strategies are ranked based on degree of certainty. In yet another embodiment, the at least two strategies comprise at least two medical diagnostic assays. In one embodiment, the at least two strategies are ranked based on minimum average cost to perform the at least two medical diagnostic assays. In yet another embodiment, the at least two strategies are ranked based on the projected time to perform the at least two medical diagnostic assays. In another embodiment, the any one decision tree algorithm is selected from among a group of algorithms, the algorithms specific to hereditary diseases comprising breast cancer, colorectal cancer, lung cancer, prostate cancer, retinoblastoma, and hereditary hemorrhagic telangiectasia. In an alternative embodiment, the received information comprises the historical frequency distribution of mutations that relate to a disease and the assays required to render a diagnosis for the disease.

The invention further relates to a system for testing for mutations in DNA, said system comprising a system for determining an optimal test order for diagnosing mutations in DNA that relate to a disease, comprising a computing environment, an input device, connected to the computing environment for receiving information, an output device, connected to the computing environment, for presenting information and a plurality of decision tree algorithms selectively executed based on at least a portion of the received information, wherein any one of the decision tree algorithms scores at least a portion of the received information and determines the optimal test order associated with the any one decision tree algorithm if the score reaches or passes a threshold, wherein the optimal test order is presented via the output device. In another embodiment, the system for testing for mutations in DNA, said system comprises a system for determining an optimal test order for diagnosing mutations in DNA that relate to a disease further determines the projected costs for each test associated with the optimal test order if the score reaches or passes a threshold, wherein projected costs are presented via the output device. In yet another embodiment, the system for testing for mutations in DNA, said system comprising a system for determining an optimal test order for diagnosing mutations in DNA that relate to a disease further determines the projected times for each test associated with the optimal test order if the score reaches or passes a threshold, wherein projected costs are presented via the output device.

The present invention further relates to a method of determining the optimal test order for diagnosing mutations in DNA that relate to a disease comprising the steps of receiving, through an input device, data indicative of the historical frequency distribution of mutations in DNA that relate to a disease and the assays required to render a diagnosis for the disease creating a history database, the database comprising a sequence of records based on the data, receiving through an input device, new data indicative of the historical frequency distribution of mutations in DNA that relate to a disease and the assays required to render a diagnosis for the disease, applying a match pattern to the history database, generating a recommendation if a frequency value of matched records located by applying the match pattern satisfies a match threshold, and communicating the recommendation through an output device. In one embodiment, applying a match pattern comprises the steps of accessing a set of records within the history database by use of a time window, the time window comprising a range of pre-selected dates, comparing the match pattern to each of the accessed records and calculating the frequency value from the matched records identified by the comparing step. In another embodiment, the match threshold is representative of a pre-selected minimum number of records corresponding to the match pattern.

The invention also relates to a method for testing for mutations in DNA, said method performed in accordance with the method of determining the optimal test order for diagnosing mutations in DNA that relate to a disease comprising the steps of receiving, through an input device, data indicative of the historical frequency distribution of mutations in DNA that relate to a disease and the assays required to render a diagnosis for the disease, creating a history database, the database comprising a sequence of records based on the data, receiving, through an input device, new data indicative of the historical frequency distribution of mutations in DNA that relate to a disease and the assays required to render a diagnosis for the disease, applying a match pattern to the history database, generating a recommendation if a frequency value of matched records located by applying the match pattern satisfies a match threshold and communicating the recommendation through an output device.

It will also be appreciated that the system may or may not contain a computing environment.

BRIEF DESCRIPTION OF THE DRAWINGS

Preferred embodiments of the invention will be described in relation to the drawings in which.

This figure depicts a decision tree for comparing two assays (i and j), given one of three prior search histories, shown here as entry points, No Prior information, Partial Heterozygous, and Partial Homozygous. Table 1 counts paths and costs along each path, and defines the notations used in the figure.

Figure 2:
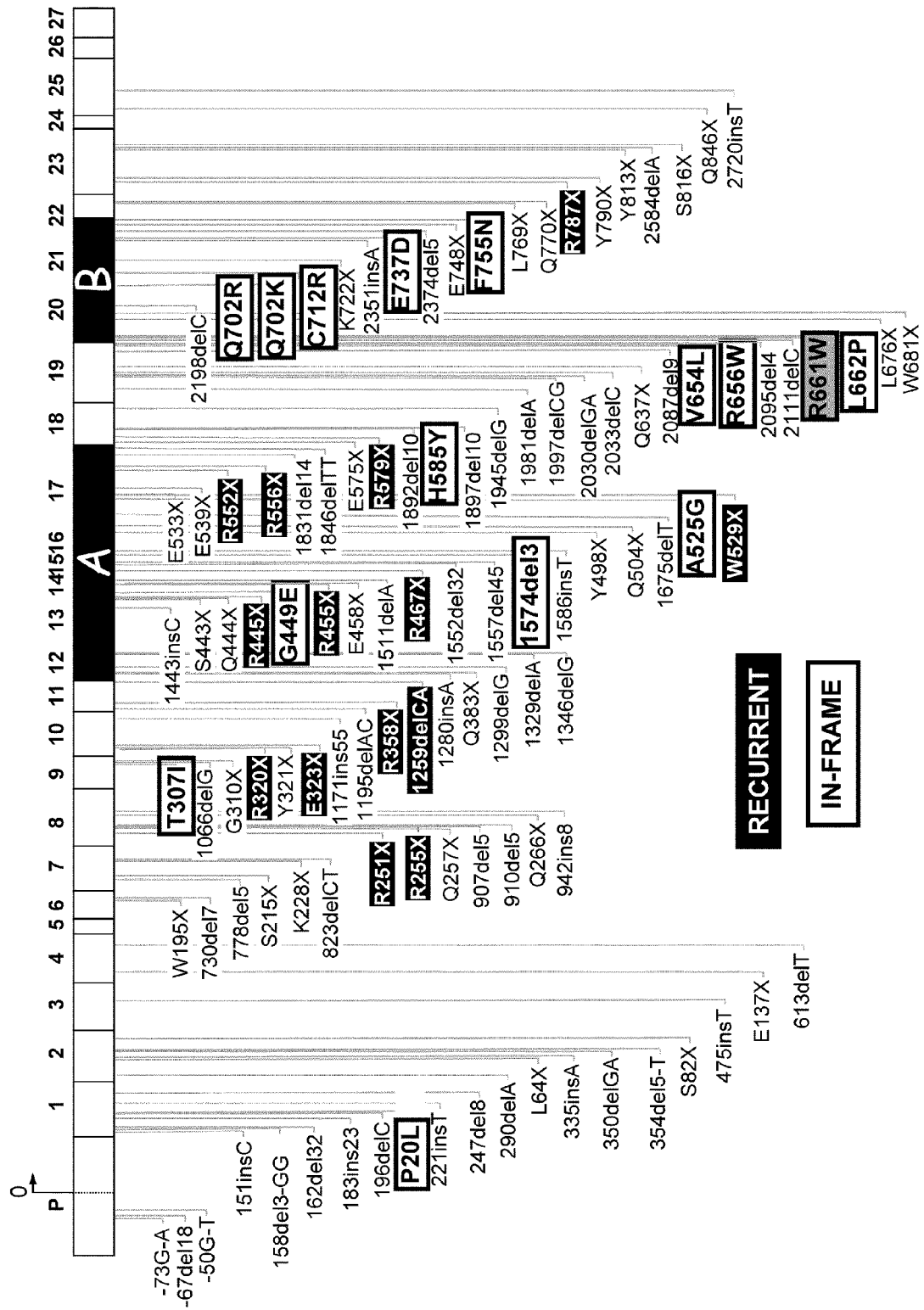

FIG. 2. Distribution within the RB1 cDNA and promoter of 111 different missense, small insertions and deletions in the germline of 165 persons. Ninety-five families had unique mutations. Fourteen recurrent mutations that affected 70 independent families are in black; fourteen in-frame mutations are outlined in black; R661W is both recurrent (6 occurrences in germline) and in-frame, indicated by a wide black border.

Figure 3:
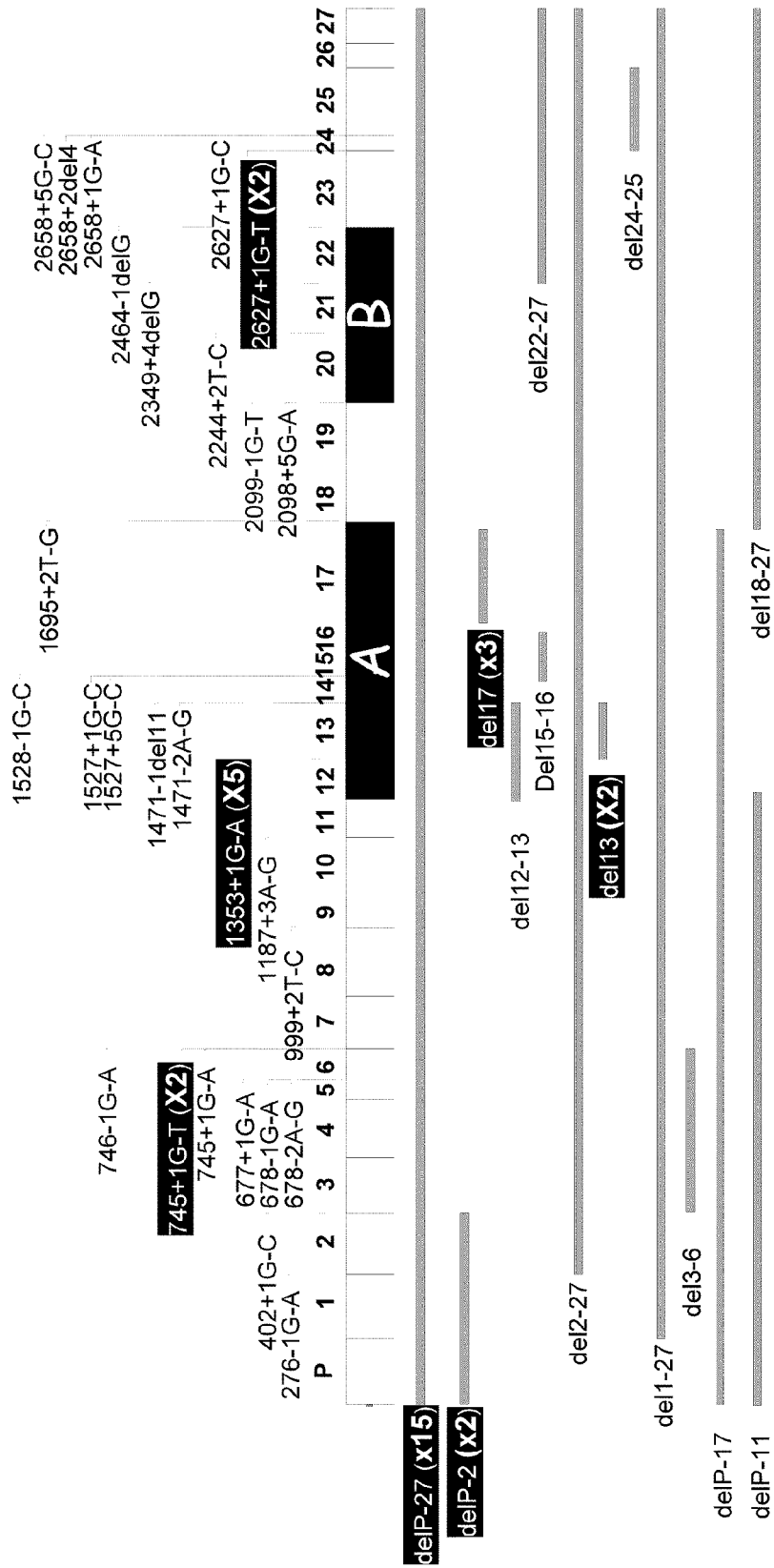

FIG. 3. Distribution within the RB1 cDNA and promoter of 41 splicing mutations and large deletions identified in the germline of 65 retinoblastoma probands. The mutations in black occurred in more than one independent family; the number of occurrences is in brackets.

Figure 4:
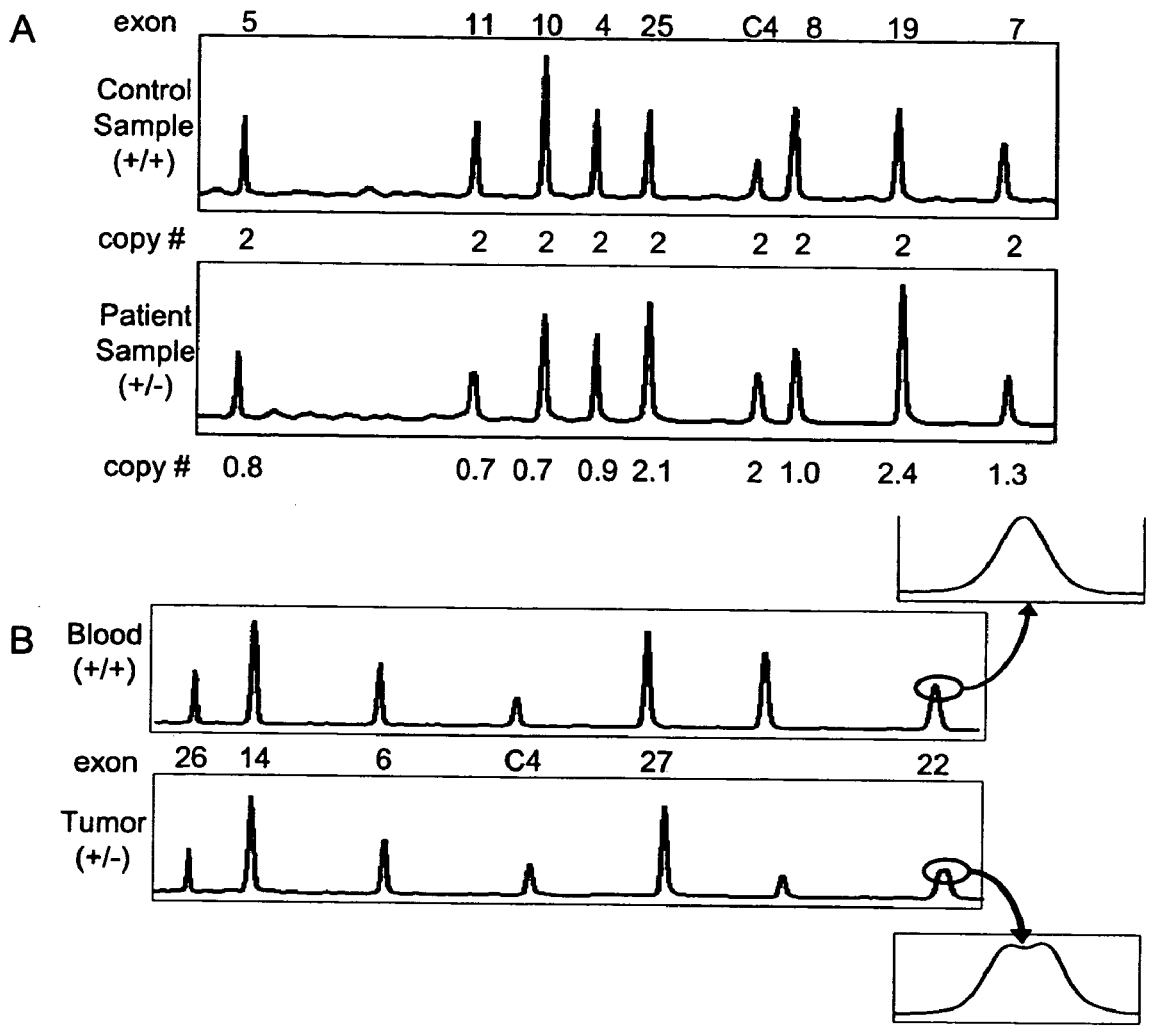

FIG. 4. Mutation detection using QM-PCR. (A) detection of a multi-exonic deletion, and (B) detection of a 2 by deletion in exon 22 by QM-PCR.

Figure 5:
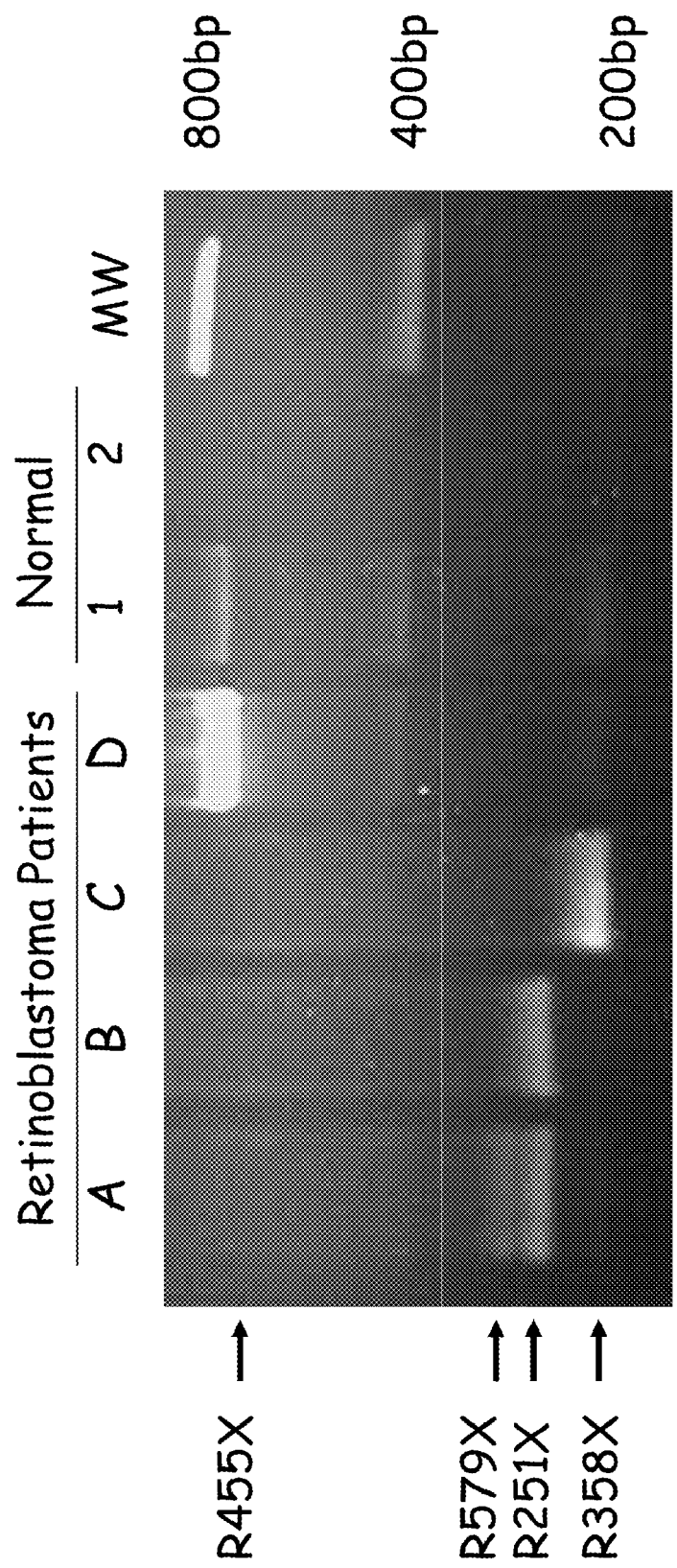

FIG. 5. Multiplex Allele Specific PCR (AS4-PCR) for rapid detection of recurrent mutations in RB1. Four samples from retinoblastoma patients (patients A-D) and two control normal samples were tested by AS4-PCR containing primers specific for recurrent mutations R455X (730 bp), R579X (287 bp), R358X (251 bp) and R251X (202 bp). Strong amplification occurred when the mutation identified by the specific PCR primer was present. Normal 1 and patient sample D also show low levels of cross hybridization to the wild-type alleles with the primers for R455X and R358X.

Figure 6:
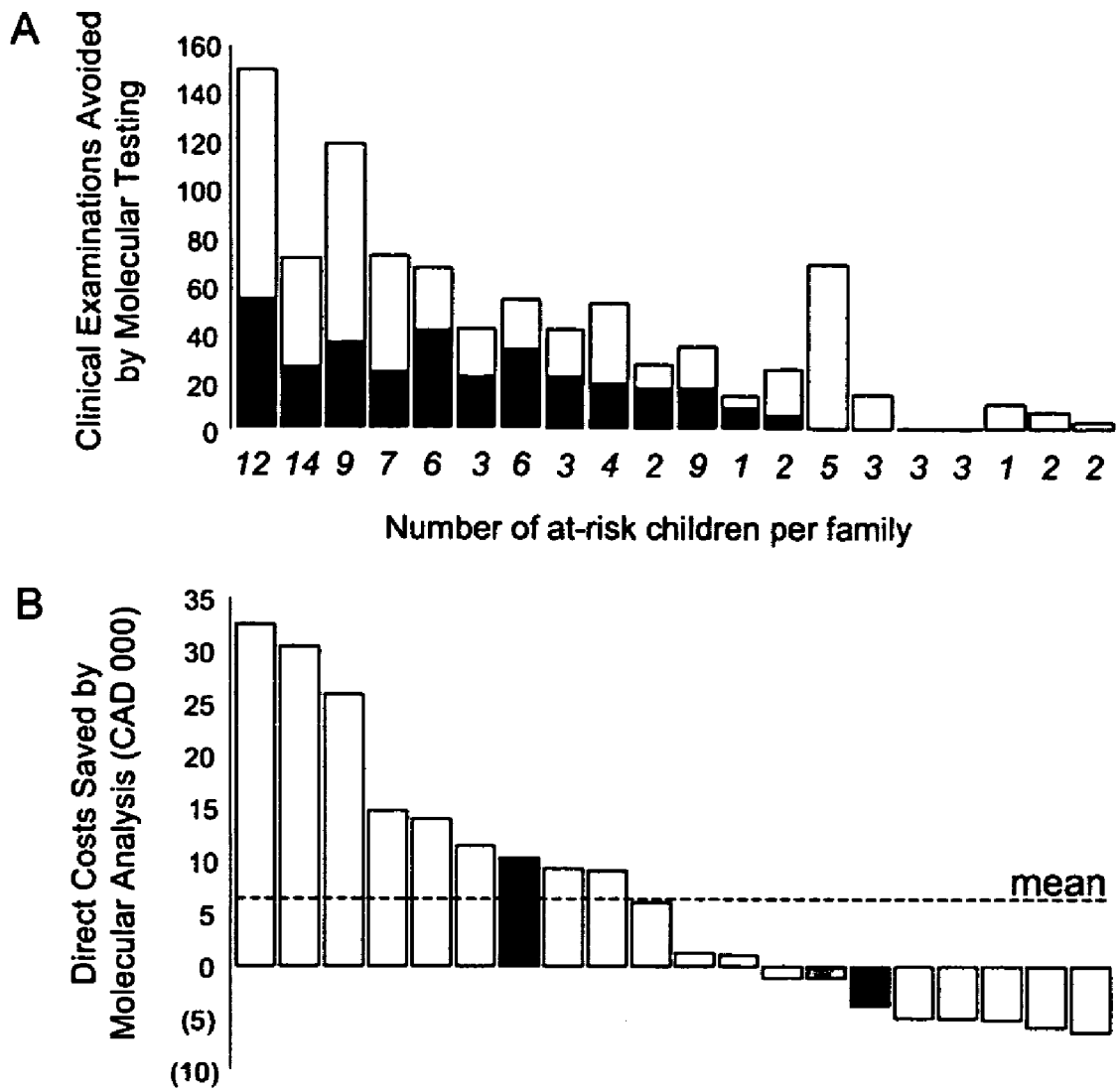

FIG. 6. Impact of molecular RB1 testing. (A) Histograms of the number of examinations avoided because of molecular results. Clinic examinations are shown in open bars, EUAs in black bars. (B) Histogram of direct surveillance costs saved for 20 families because of molecular RB1 testing. Mean savings was CAD 6591 per family (horizontal line). Bilateral and familial retinoblastoma families are shown in open bars, unilateral non-familial families in bars with oblique hatches. The molecular strategy cost more than conventional surveillance for two families in which all assays failed to show the proband's mutation (speckled bars) and for six families in which at-risk family members were few in number or significantly older than the proband.

DETAILED DESCRIPTION

In this document the following terminology is adopted.

Decision tree—a list of all medical diagnostic assays that may be applied to the DNA, RNA or protein of a person to achieve a diagnosis; and for each such assay, all possible outcomes; and for each such outcome, all subsequent actions that may be applied to achieve a diagnosis, such as to perform a particular assay or to stop analysis.

Entry point—a state of knowledge that initiates the decision tree

Exit point—a state of knowledge that requires continued analysis to reach a conclusive diagnosis.

Stopping Point—a state of knowledge that allows conclusive diagnosis or otherwise ends the search for mutations.

Strategy—an ordered series of actions through a decision tree that leads from an entry point to a stopping point, in which each choice may depend on information obtained from prior choices, outcomes and conditional probabilities of future outcomes.

Search Path—a sequence of actions and outcomes from an entry point to an exit point, but not necessarily a stopping point.

Search History—a partial search path that includes a starting point, but not necessarily an exit point.

Medical Diagnostic Assay—manipulation of a human tissue sample or human bodily fluid sample that causes information to be revealed about the sample that is useful to diagnose the disease status of the sample's donor. Examples of medical diagnostic assays include, but are not limited to, amplification by polymerase chain reaction of sample DNA or sample mRNA to determine the sequence of DNA bases; amplification by polymerase chain reaction of sample DNA or sample mRNA to detect deletion or duplication of coding exons; and in-situ hybridization by a series of fluorescent-labelled probes viewed under a fluorescent microscope.

Cost—any measurable consequence of performing a medical diagnostic assay. Costs include, but are not limited to, the cash expenditures required to perform a medical diagnostic assay, the time required to perform a medical diagnostic assay, and a weighted average of cash expenditures and time required to perform a medical diagnostic assay.

Input device—examples of input devices include any one or more of a keyboard, a scanner, a user pointing device, such as, for example, a mouse, a touch pad, or an audio input device or a video input device, or any device, electronic or otherwise which can be utilized for inputting or entering data or information.

Output device—examples of output devices include a printer, a display, a transmitter, a modem, or any other device that can be used to output data.

Computing Environment—A computing environment can be defined as the processing components of a computer-based system which accepts input entered with an external input device connected to the said processing components, and presents processing results to an external output device. It includes a single computer, and a network of computers. The input device is connected to a network of computers (the computing environment) via a network connection, which may be either a dial-up connection using a modem (the public switched telephone network, cable, or satellite) or via a dedicated data circuit. The network can be a public network, like the Internet, or a closed, private data network, such as an in-house network or an intranet. The computers of the network may be organized in a client-server or peer-to-peer fashion. A computing environment also includes software for execution on the computer(s), for example, communications software in the case of a network configuration, and database software for implementing and accessing a database.

Computer-readable medium—examples of computer readable media include recordable-type media such as floppy disc, a hard disk drive, RAM, and CD-ROM's, as well as transmission-type media, such as digital and analog communications links.

Database—the data or information stored in the database can also be updated by, or dynamically linked to, various external sources, including but not limited to news services, research publications, research facilities, healthcare laboratories, providers of healthcare goods or services, pharmaceutical companies, research institutions, schools. The database will contain any and all information deemed necessary or desirable for providing all of the processing or services or functions described herein.

The current invention provides at least one minimum-cost sequence for medical diagnostic assays in a search for genetic mutations that relate to a disease.

Inputs to the Search

The following assumptions are made:

(a) An analyst knows the whole spectrum of mutations and the frequency with which each mutation occurs in the population. This assumption cannot always be met precisely, but in many situations, the population distribution can be approximated by a large sample of previously discovered mutations.

(b) For each mutation in the population, the analyst can specify a set of medical diagnostic assays that provides a conclusive diagnosis.

(c) The analyst knows the cost of each step required to diagnose mutations relating to a disease.

(d) The analyst can measure the benefit of a diagnosis, conditional on the outcomes of the medical diagnostic assays performed.

Optimal Test Order

The first two assumptions ensure existence of a joint probability distribution for mutations that diagnose disease over the field of all (sub) sets of assays. For any n medical diagnostic assays, $2^n$ distinct strategies are possible. From the assumptions above, the analyst has enough information to rank strategies.

The Net Cost Measure that Ranks Strategies

The assumptions above provide enough information to calculate the likelihood that a search will proceed along each possible path, the cost of any path, and the projected cost over all paths. Calculate the cost measure used to rank test orders as follows:

$$\text{Strategy Expected Cost} = \sum_{j=1}^{N} P_j \sum_{i=1}^{T_j} (C_{ij} - B_{ij}) \quad (1)$$

where $C_{ij}$, is the cost of the i'th action performed along the j'th feasible search path; $B_{ij}$ is the value of all incremental benefits attained by the i'th action performed along the j'th feasible search path; $T_j$ is the total number of actions on search path j; N is the number of feasible search paths generated by the particular strategy; and $p_j$ is the likelihood that the search path j occurs. The incremental benefits, assumed to be known, include all direct consequences of successful diagnosis, such as cost savings from eliminating unnecessary treatment or intensive screening when an individual is shown not to carry a predisposition to heart disease. This cost measure is equally valid for a partial search path, such as a history, as for a full search path.

The set of probabilities $\{p_j\}$ is approximated by the frequency distribution of empirically observed outcomes. As medical diagnostic assays reveal new information, frequencies should be updated to ensure accuracy, until sample sizes grow so large that no significant changes are observed in the set of probabilities.

Solutions

To find a strategy that minimizes the Strategy Expected Cost measure (an optimal strategy), follow the process of pairwise comparisons detailed below. If more than one optimal strategy exists, the multiplicity of solutions is trivial because each valid solution has the same average cost. The procedure to find an optimal strategy follows:

a) For each feasible strategy generated by a decision tree, find the last decision preceding each stopping point in the decision tree. Calculate the projected cost for each feasible partial strategy that starts at the decision. If the projected cost of each such partial strategy is positive, replace the decision with a stopping point, ensuring no incremental benefits and no further costs.

b) Proceed by backwards iteration from the decisions closest to stopping points in each minimum-cost strategy to the first decision, calculating the projected cost from each decision forward in the tree and eliminating all partial strategies with positive projected cost. When all decisions have been evaluated for all feasible strategies, the decision tree has been refined.

c) From the refined decision tree, pick any feasible strategy and call it the current strategy.

d) Use the Strategy Expected Cost measure (1) to find the projected cost of the partial strategy that includes only the first two assays in the current strategy. Compare this result to the projected cost of the partial strategy formed by the same two assays in reverse order. Alter the current strategy to include the order for the two assays that achieves the lowest cost, with all other actions unchanged. These two assays are now ranked.

e) Use the cost measure (1) to compare the projected cost to perform the partial strategy formed by first three assays in the current strategy with the projected cost of the partial strategy formed when the second and third assays are in reverse order. Retain as the current strategy the order that achieves the lowest cost, with all other actions in the strategy unchanged. If this comparison causes the order of assays to change, then all assays that change order and all that follow are unranked and the analyst returns to step (d). If the current strategy is not changed by the cost comparison, the second and third assays are ranked and the analyst proceeds to step (f).

f) Consider the last assay already ranked and the first assay not yet ranked. Compare the projected cost of two partial strategies formed when these two assays are in the current order and in reverse order. Retain the partial strategy that achieves the lowest projected cost, and leave all other decisions unchanged. If the cost comparison changes the assay ordering, the two assays in consideration and all assays that follow are now unranked. If the ordering does not change, then all preceding assays and the two last considered are all ranked. Repeat this step iteratively until all assays in the optimal path are ranked.

g) When all assays in a strategy are ranked, the strategy is optimal and it must achieve minimal projected cost.

Example 1

Unilateral Retinoblastoma Probands

Retinoblastoma is a rare, malignant eye tumor that occurs only in infants, affecting approximately one out of every 15,000 live births. Males have a higher incidence than females (1.7 to 1). There are no geographical or racial associations with retinoblastoma, suggesting that environmental factors do not play a causal role in the development of this disease. Untreated, retinoblastoma can metastasize from the eye through the optic nerve to the brain. Left untreated, 98% of patients with retinoblastoma die, typically within the first four years of life. Treatment may mean blindness or the loss of one or both eyes and patients who survive treatment of retinoblastoma are at elevated risk for secondary non-ocular cancers.

Retinoblastoma is a paradigm of Knudson's two-hit hypotheses. Each cell has two copies of DNA, one from each parent. If a child inherits a defective copy of the RB1 gene, or undergoes a mutation early in the process of cell differentiation, the child has only one functioning tumor suppressor gene. Further mutation in the retinal cells of a person who inherits a defective RB1 gene leads to retinoblastoma.

In 60% of cases, retinoblastoma affects only one eye. Unilateral cases of retinoblastoma are usually diagnosed in the second year of life. In 40% of affected children, retinoblastomas affect both eyes. Bilateral retinoblastomas are often multifocal—that is they have many distinct tumor foci. Bilateral cases are generally diagnosed earlier, usually in the first year of life.

A molecular diagnosis for unilateral retinoblastoma requires the location of two mutations in DNA extracted from tumor cells. It is important also to know whether a mutation that causes retinoblastoma is carried in the person's germline cells and can be inherited. Therefore, DNA extracted from blood is tested for mutations found in tumor DNA. Diagnosis is not complete unless a mutation found in tumor DNA is also found in DNA extracted from blood, or unless two mutations are found in tumor DNA and neither are found in blood DNA.

Decision Tree to Rank Two Assays for Retinoblastoma

Figure 1:
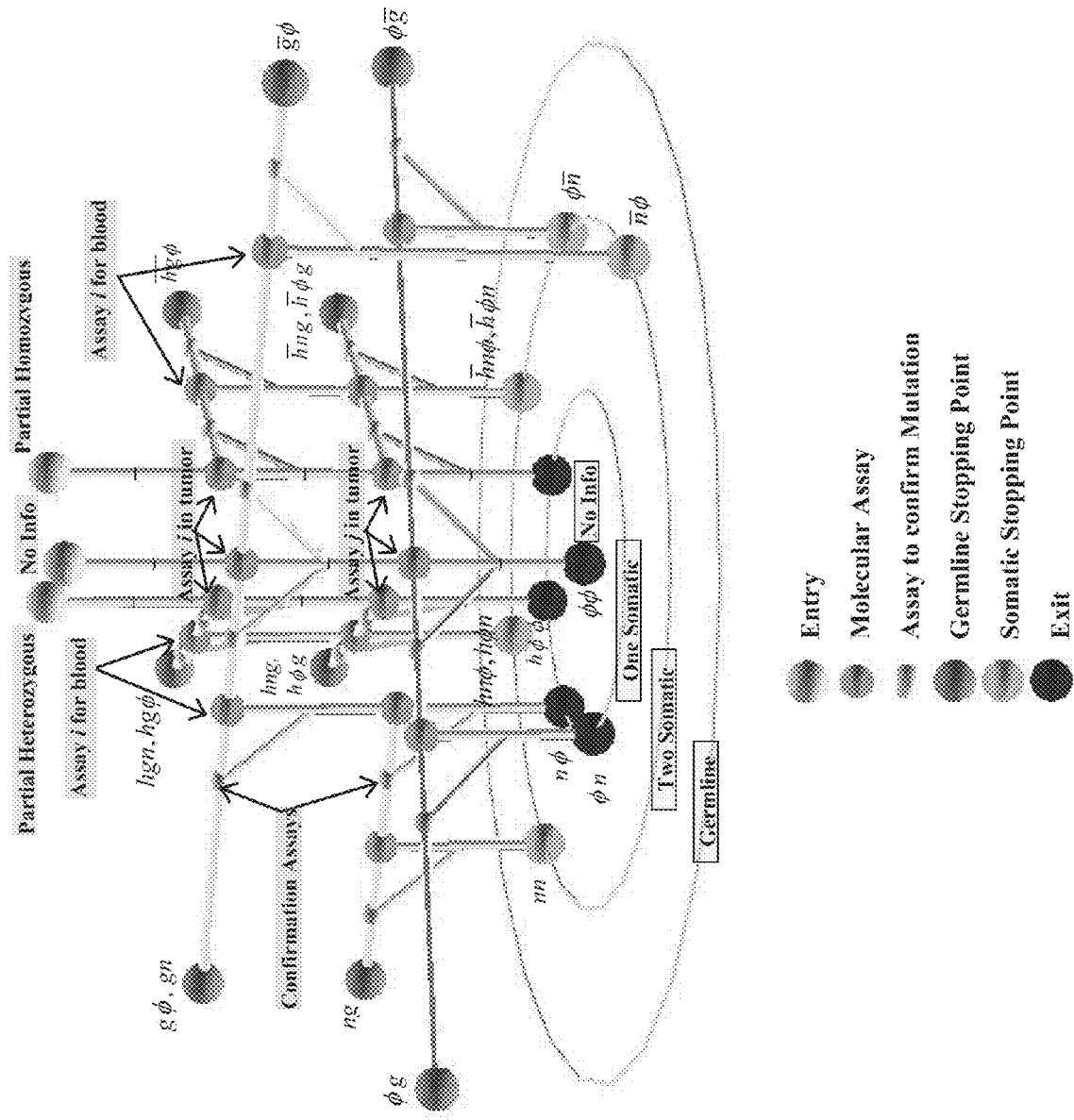
FIG. 1. HOPE for Unknown Unilateral Mutations

The figure below depicts a decision tree for comparing two assays (i and j), given one of three prior search histories, shown here as entry points, No Prior Information, Partial Heterozygous, and Partial Homozygous (FIG. 1). Table 1 counts paths and costs along each path, and defines the notation used in FIG. 1.

How to Rank Strategies

For two arbitrary assays i and j, the third column of Table 1 gives the incremental costs of performing i before j and the fourth column gives the costs of performing j before i. The projected cost of each test order equals the vector product of the probabilities in the first column and the costs in the third or fourth column, respectively. To simplify the presentation, path-dependent costs have only the last step in the history shown as arguments. For example, $C_i(j)$ means the cost to confirm a mutation shown by i when i follows j.

To order two tests, given any history, compare the projected cost of testing in order (i, j) and in order (j, i). The expression below is the reduced form of the difference between the projected costs of test order (i, j) over test order (j, i). If this amount is negative, then (i, j) dominates (j, i), and if it is positive, (j, i) dominates (i, j).

$$CostDiff =$$
$$(ng)C_i - (gn)C_j + (2ng + \varphi\bar{n} + \varphi g + \varphi\bar{g}\_h\varphi g + h\varphi n + h\varphi\bar{g} + h\varphi\bar{n})T_i -$$
$$(2gn + \bar{n}\varphi + g\varphi + \bar{g}\varphi + hg\varphi\_\overline{hg}\varphi + \overline{hn}\varphi)T_j +$$
$$\begin{pmatrix} nn + 2gn + n\varphi + \bar{n}\varphi + 2g\varphi + 2\bar{g}\varphi + \\ 2hg\varphi + hn\varphi + 2\overline{hg}\varphi + \overline{hn}\varphi \end{pmatrix}[C_i - C_i(j)] -$$
$$\begin{pmatrix} nn + 2ng - \varphi n + \varphi\bar{n} + 2\varphi g + 2\varphi\bar{g} + \\ 2h\varphi g + h\varphi n + 2\overline{h}\varphi\bar{g} + 2\overline{h}\varphi\bar{n} \end{pmatrix}[C_j - C_j(i)]$$

TABLE 1

Paths and Costs for Unilateral Retinoblastoma

| Path | Description | Cost, Order (i, j) | Cost, Order (j, i) |
|---|---|---|---|
| Nn | both hetero non-germline | $2(T_i + T_j) + C_i + C_j(i)$ | $2(T_i + T_j) + (j) + C_j$ |
| Ng | hetero non-germline, hetero germline | $C_i + 2(T_i + T_j + C_j(i))$ | $2(T_j + C_j)$ |
| Gn | hetero germline, hetero non-germline | $2(T_i + C_i)$ | $C_j + 2(T_j + T_i + C_i(j))$ |
| nφ | hetero non-germline, none | $2T_i + C_i + T_j$ | $2T_j + C_i(j) + T_j$ |
| n̄φ | homo non-germline, none | $2T_i + C_i$ | $T_j + 2T_i + C_i(j)$ |
| gφ | hetero germline, none | $2(T_i + C_i)$ | $T_j + 2(T_i + C_i(j))$ |
| ḡφ | homo germline, none | $2(T_i + C_i)$ | $T_j + 2(T_i + C_i(j))$ |
| φφ | none, none | $T_i + T_j$ | SAME |
| φn | none, hetero non-germline | $T_i + 2T_j + C_j(i)$ | $T_i + 2T_j + C_j$ |
| φn̄ | non, homo non-germline | $T_i + 2T_j + C_j(i)$ | $2T_j + C_j$ |
| φg | none, hetero germline | $T_i + 2(T_j + C_j(i))$ | $2(T_j + C_j)$ |
| φḡ | none, homo germline | $T_i + 2(T_j + C_j(i))$ | $2(T_j + C_j)$ |
| hgφ | prior hetero; hetero germline i | $2(T_i + C_i)$ | $T_j + 2(T_i + C_i(j))$ |
| hφg | prior hetero; hetero germline j | $T_i + 2(T_j + C_j(i))$ | $2(T_j + C_j)$ |
| hnφ | prior hetero; hetero non-germline i | $2T_i + C_i$ | $T_j + 2T_i + C_i(j)$ |
| hφn | prior hetero; hetero non-germline j | $T_i + 2T_j + C_j(i)$ | $2T_j + C_j$ |
| hφφ | prior hetero; none in both i and j | $T_i + T_j$ | SAME |
| h̄gφ | prior homo; homo germline i | $2(T_i + C_i)$ | $T_j + 2(T_i + C_i(j))$ |
| h̄φg | prior homo; homo germline j | $T_i + 2(T_j + C_j(i))$ | $2(T_j + C_j)$ |

TABLE 1-continued

Paths and Costs for Unilateral Retinoblastoma

| Path | Description | Cost, Order (i, j) | Cost, Order (j, i) |
|---|---|---|---|
| $\overline{hn}\phi$ | prior homo; homo non-germline i | $2T_i + C_i$ | $T_j + 2T_i + C_i(j)$ |
| $\overline{h}\phi\overline{n}$ | prior homo; homo non-germline j | $T_i + 2T_j + C_j(i)$ | $2T_j + C_j$ |
| $\overline{h}\phi\phi$ | prior homo; none in both i and j | $T_i + T_j$ | SAME |

This pairwise comparison is the kernel of the iterative process that compares projected costs. Used iteratively, it identifies an optimal strategy. If an empirical sample is used to implement this procedure rather than a known joint probability distribution, it is useful to recalculate frequencies in the table each time the accumulated sample changes, before comparing differential costs. Sample size is key to whether variation in the observed data will affect how accurately the process functions. With large sample sizes (hundreds of mutations), it is generally safe to assume that variations in outcomes are very small in comparison to the whole sample.

The ranking statistic CostDiff has an intuitive interpretation. The first two terms count the cost of testing first by i when, in fact, j provides information that concludes the search, such as the discovery of a germline mutation. Similarly, the last two terms count the cost of testing first by j when, in fact, test i resolves the search. In two states, ng and gn, the marginal test costs are doubled because the first test reveals a homozygous mutation in tumor tissue but not in the patient's blood, and then second test reveals a germline mutation, which concludes the search.

Example 2

Screening for RB1 and BRCA Mutations

A sensitive and efficient strategy is presented to screen retinoblastoma probands for RB1 mutations. The method combines quantitative multiplex PCR (QM-PCR), two-dye double-exon sequencing, and for unilateral tumors, methylation-sensitive PCR (MS-PCR). The potential of allele-specific PCR (AS4-PCR) to increase efficiency was also evaluated. The current invention is used to model the search problem and derive optimal orderings of 19 different tests for two proband groups: bilateral and familial unilateral probands, and sporadic unilateral probands. Efficient use of molecular testing reduced the estimated surveillance cost for 20 randomly selected retinoblastoma families.

Using a combination of molecular techniques, 452 RB1 mutations were detected in clinical samples from 382 probands with retinoblastoma (Table 2).

TABLE 2

Characterization of 452 mutant RB1 alleles from 382 retinoblastoma probands.

| | BILATERAL Germline Studied Blood | | | | | UNILATERAL Sporadic Studied Tumor | | | | | |
|---|---|---|---|---|---|---|---|---|---|---|---|
| | Bilateral Germline | | Unilateral Germline | | | Mutant Alleles | "Somatic" M1/M2 | | Tumors | | |
| MUTATION TYPES | Bilateral | % M1 found | Familial | Non-Familial | % M1 found | in Tumors | # with LOH | % | with LOH Count | (%) | Total Count |
| Null Mutations | | | | | | | | | | | |
| Whole gene deletions (P to 27) | 11 | 6% | 0 | 4 | 13% | 33 | 29 | 13% | 6/26 | 23% | |
| Exonic deletions | 14 | 7% | 0 | 0 | 0% | 18 | 18 | 8% | 3/11 | 27% | |
| Small deletions or insertions | 47 | 24% | 4 | 2 | 20% | 42 | 40 | 18% | 13/21 | 62% | |
| ≦2 bases from splice junction | 25 | 13% | 1 | 2 | 10% | 21 | 19 | 8% | 5/10 | 50% | |
| >2 bases from splice junction | 5 | 3% | 0 | 0 | 0% | 0 | 0 | 0% | 0/0 | n/a | |
| Nonsense mutations | 84 | 42% | 2 | 2 | 13% | 95 | 93 | 41% | 29/45 | 64% | |
| Total | 186 | 93% | 7 | 10 | 57% | 209 | 199 | 89% | 56/113 | 50% | 402 |
| In-Frame (not truncating) | | | | | | | | | | | |
| Deletion 3 bp, exon 4, 13, 24-25 | 2 | 1% | 2 | 0 | 7% | 2 | 2 | 1% | 1/1 | 100% | |
| In-frame splice deletions | 0 | 0% | 0 | 0 | 0% | 0 | 0 | 0% | 0/0 | n/a | |
| Missense Mutations | 10 | 5% | 7 | 3 | 33% | 8 | 5 | 2% | 2/4 | 50% | |
| Total | 12 | 6% | 9 | 3 | 40% | 10 | 7 | 3% | 3/5 | 60% | 31 |
| Promoter Mutations | | | | | | | | | | | |
| Promoter Sequence Mutations | 1 | 1% | 1 | 0 | 3% | 0 | 0 | 0% | 0/0 | n/a | |
| Methylation | 0 | 0% | 0 | 0 | 0% | 17 | 17 | 8% | 7/8 | 88% | |
| Total | 1 | 1% | 1 | 0 | 3% | 17 | 17 | 8% | 7/8 | 88% | 19 |
| | | | | | | Tumors with LOH | | | 66/126 | 52% | |

TABLE 2-continued

Characterization of 452 mutant RB1 alleles from 382 retinoblastoma probands.

| | BILATERAL Germline Studied Blood | | | | | UNILATERAL Sporadic Studied Tumor | | | | | |
|---|---|---|---|---|---|---|---|---|---|---|---|
| | Bilateral Germline | | Unilateral Germline | | | Mutant Alleles | "Somatic" M1/M2 | | Tumors | | |
| MUTATION TYPES | Bilateral | % M1 found | Familial | Non-Familial | % M1 found | in Tumors | # with LOH | % | with LOH Count | (%) | Total Count |
| Number of Probands Analyzed | 224 | | 20 | n/a | | | 134 | | | | 378 |
| Number of Probands Diagnosed | 199 | 100% | 17 | 13 | 100% | | 112 | | | | 328 |
| Sensitivity (diagnose proband) | 89% | | 85% | | | | | 84% | | | 87% |
| Number of Alleles Examined | 224 | | 20 | 24 | | 266 | 242 | | | | 510 |
| # of mutant alleles (with LOH) | 199 | | 17 | | | 236 | 223 | 100% | | | 452 |
| # of mutant alleles (not LOH) | 199 | | 17 | 13 | | 170 | 157 | | | | 399 |
| Sensitivity (identify allele) | 89% | | 85% | | | 88.7% | 92% | | | | 89% |

A review was previously published of 368 reported RB1 mutations, including 27 unique mutations, [Lohmann, 1999]. It can be confirmed that mutations likely to result in residual protein (missense mutations, in-frame deletions and splice abnormalities and promoter mutations) are rare (7%) in bilaterally affected probands, but represent 43% of mutations in unilateral probands. Neither of the previous studies reports whole-exon or multi-exon deletions, which account for 14% of the bilateral probands in this study. It is likely that the techniques used in these studies were insensitive to exon copy number. Karyotype analysis will detect 5-7% of RB1 mutations that are large rearrangements, but has insufficient resolution for small exonic deletions.

Thirteen of fifteen missense mutations are clustered in the NB pocket and the intervening spacer region, confirming that in-frame mutations favour critical regions of RB1. At least three of the missense mutations have been associated with reduced penetrance (R661W, V654L and C712R) (DiCiommo et al. 2000). Only one of the missense mutations was recurrent, R661W. In addition, the mutations identified in the germline of unilaterally affected children, 43% of which are in-frame, can also be considered to have reduced penetrance. The recurrent mutations, including R661W, all involve C→T transitions (FIG. 1), usually resulting in CGA (arginine) mutating to TGA (STOP). Of 46 arginine codons in RB1, 14 are encoded by CGA/G, and 13 of 14 are targets for recurrent mutations.

Exons have been screened for mutations using a variety of techniques including single strand conformation polymorphism (SSCP) analysis, DGGE [Blanquet, 1995], heteroduplex analysis, Southern blotting, or pulsed field gel electrophoresis [Janson, 1994]. Aside from direct sequencing of exons, the majority of these methods rely on an initial exon screen followed by sequencing of suspect amplified fragments. Double-exon sequencing is used without a pre-screen for exonic changes and found that this could be an efficient approach when used together with the instant invention.

Detection of RB1 mutant alleles has required the analysis of genomic DNA, because in blood mRNA from null alleles was undetectable [Dunn, 1989]. This has been attributed to message instability due to NMD [Hentze, 1999]. The null alleles however are easily detected in mRNA in retinoblastoma tumors. This may occur either because the absence of pRB leads to up-regulation of transcription to levels where even degrading mRNA is detectable by PCR [Dunn, 1989], because the mRNA was prepared for tumor cell lines without time for NMD to be active, or perhaps because NMD is less active in tumors. Stabilization of mRNA showing premature truncation of translation by puromycin or cycloheximide [Carter, 1995] prior to RT-PCR might allow detection of mRNA from null alleles in blood, adding efficiency and a potential increase in sensitivity of RB1 mutation identification.

The current invention provides a practical tool to evaluate prospective new tests. For example, the impact of developing multiplex AS4-PCR on the sensitivity, costs and turnaround time was assessed prospectively prior to using the assay on clinical samples. The analysis showed that AS-PCR would only be more effective than direct sequencing if multiple point mutations with relatively high frequency of occurrence were assayed in a single reaction. Thus, AS4-PCR is implemented only after finding a combination of experimental conditions that allowed four recurrent nonsense mutations to be multiplexed and detected in a single agarose gel. If the 13 mutations that have occurred 4 or more times were tested together in one or two multiplex reactions, 114/401 (28%) of RB1 mutations could be detected by simple PCR assays.

The optimization of multiple steps for mutation detection for large genes may be generalized to other genes which cause disease with a high frequency of private null alleles including copy number changes, such as BRCA1 and BRCA2 in breast cancer. Mutation identification for BRCA genes is similar to RB1 in that there are many ways that the genes can be mutated, and that knowledge of carrier status can provide very real advantages to the family [Kutner, 1999]. However, there is a larger impact of founder mutations that can be specifically targeted in mutation identification. The copy number changes that are detected readily with QM-PCR are common in the BRCA genes [Gad, 2001], but are not commonly incorporated into screening strategies [Hegde, 2000].

A very important component of RB1 mutation identification is the sensitivity of the assays to discover the mutant allele(s) in the probands or their tumors. Without high sensitivity, the social and technical cost of attempting the molecular work is high when the mutant allele is not identified. The current invention provides 90% sensitivity to identify RB1 mutant alleles, the highest yet reported. Others indicate sensitivity to identify mutant RB1 alleles between 40% [Sippel, 1998] and 80% [Lohmann, 1999]. Linkage studies indicate that the unidentified mutant alleles in hereditary retinoblastoma probands still involve the RB1 gene, even when mutations are not found. When all assays have been negative, failure to identify a mutant allele was reported to the referring professionals and work continued to identify the RB1 mutation on a research basis.

Intronic translocations, which remain undetectable by our current techniques, may account for some of the 10% of families for which no mutation was identified. Fluorescent in-situ hybridization (FISH), a method well suited to the detection of translocations, has not yet revealed any translocations in samples where all of the assays were negative.

The use of the current invention to optimize RB1 mutation detection decreases test costs, decreases turnaround time and increases the likelihood of clinical implementation. This invention is applicable to other genetic diseases, such as, breast cancer, colorectal cancer, lung cancer, prostate cancer, retinoblastoma, and hereditary hemorrhagic telangiectasia, and to general cost impact assessment of new techniques before implementation.

Clinical Impact of RB1 Mutation Identification

Cost of conventional clinical screening was compared to cost of molecular analysis in the management in retinoblastoma families. For each Ontario proband whose RB1 mutation had been determined by molecular analysis, age for relatives at risk was calculated at i) time of diagnosis in proband and ii) time at which RB1 mutation was identified. Direct health care costs were estimated depending on the age of proband and each child (<7 years) relative. Costs of conventional clinical surveillance for retinoblastoma at the Hospital for Sick Children, Toronto, estimated in 1994 [Noorani, 1996], were compared to the molecular test costs in the same year. Conventional clinical surveillance costs were adjusted for inflation between 1994 and 2002 and compared to the calculated 2002 molecular test costs with full optimization.

Mutation Types and Recurrent Mutations

All functional classes of mutations were identified (Table 2).

The germline mutations in 199 bilateral probands were 93% null, 6% in-frame and 1% occurred in the promoter region. The germline mutations identified in 30 unilateral probands (both familial and non-familial) were 57% null, 40% in-frame and 3% promoter, consistent with these mutations being associated with reduced penetrance. The mutant alleles identified in retinoblastoma tumors from 113 unilaterally affected probands, but not detectable in blood and therefore presumed somatic, were 88% null, 3% in-frame and 8% methylation of the promoter.

Of 129 sporadic retinoblastoma tumors in which mutations were identified, the second allele was mutated by loss of heterozygosity (LOH) in 67 (52%). Interestingly, the likelihood that the M2 event would be LOH varied with the type of M1 event. Only 22% of tumors with M1 whole gene deletions, and only 27% of tumors with exonic deletions, showed LOH, while 89% of tumors in which M1 was methylation of the promoter showed LOH.

The distribution of 229 germline mutations is illustrated in FIGS. 2 and 3 and Table 2.

The majority (93% for bilateral probands and 57% for unilateral probands) were null mutations that predict a truncated protein or mRNA with a premature STOP codon that is anticipated to be degraded by nonsense-mediated decay (NMD) (Hentze, 1999). These null mutations, including large deletions, deletions involving one or more exons and splice mutations (FIG. 2), and small frame-shifting intra-exonic insertions and deletions, and nonsense mutations (FIG. 3), were distributed throughout the RB1 gene. Most of the missense mutations were clustered in the RB1 domains A and B, which are known to be important in the regulation of transcription by the RB1 protein product, pRB (DiCiommo et al. 2000).

The 200 somatic mutations (M2 for germline cases or M1/M2 for non-germline cases) were similarly distributed between mutation types, except that methylation of the promoter accounted for 8% of somatic mutations (Table 2). We have tested blood from 7 of 28 germline cases in which we have not found an RB1 mutation and none showed promoter methylation (data not shown).

TABLE 3

Recurrent Mutations identified by QM-PCR and bidirectional sequencing.
Recurrent Mutations identified by QM-PCR and bidirectional sequencing

| Test | Location | Mutation | Total | Somatic | Germline all | unilateral | bilateral |
|---|---|---|---|---|---|---|---|
| Small Deletions | | | | | | | |
| QM-PCR | Exon 9 | 1066delG | | | 2 | 1 | 1 |
| QM-PCR | Exon 11 | 1259delCA | | | 2 | | 2 |
| Nonsense Mutations | | | | | | | |
| sequence | Exon 10 | R320X | 18 | 6 | 12 | | 12 |
| sequence | Exon 15 | R467X | 15 | 8 | 7 | 2 | 5 |
| AS4-PCR | Exon 18 | R579X | 13 | 6 | 7 | 1 | 6 |
| AS4-PCR | Exon 14 | R455X | 11 | 7 | 4 | | 4 |
| sequence | Exon 14 | R445X | 10 | 3 | 7 | | 7 |
| AS4-PCR | Exon 11 | R358X | 8 | 3 | 5 | | 5 |
| AS4-PCR | Exon 8 | R251X | 8 | 5 | 3 | | 3 |
| sequence | Exon 23 | R787X | 7 | 3 | 4 | | 4 |
| sequence | Exon 17 | R552X | 6 | 4 | 2 | | 2 |
| sequence | Exon 8 | R255X | 4 | 1 | 3 | | 3 |
| sequence | Exon 17 | R556X | 4 | 2 | 2 | | 2 |
| sequence | Exon 23 | Y790X | 3 | 2 | 1 | | 1 |
| sequence | Exon 18 | Q575X | 2 | 2 | | | |
| sequence | Exon 10 | E323X | 2 | | 2 | | 2 |

TABLE 3-continued

Recurrent Mutations identified by QM-PCR and bidirectional sequencing.
Recurrent Mutations identified by QM-PCR and bidirectional sequencing

| Test | Location | Mutation | Total | Somatic | Germline all | unilateral | bilateral |
|---|---|---|---|---|---|---|---|
| Splice Mutations | | | | | | | |
| sequence | Exon 12 | 1353+1G→A | 7 | 2 | 5 | 1 | 4 |
| sequence | Exon 23 | 2627+1G→T | 2 | 0 | 2 | 0 | 2 |
| sequence | Exon 6 | 745+1G→T | 2 | 0 | 2 | 1 | 1 |
| Missense Mutations | | | | | | | |
| sequence | Exon 20 | R661W | 7 | 0 | 7 | 4 | 3 |
| Promoter Mutations | | | | | | | |
| methylation | Promoter | Pmeth | 11 | 11 | 0 | 0 | 0 |
| Large Deletions | | | | | | | |
| QM-PCR | | del P to 27 | 39 | 24 | 15 | 4 | 11 |
| QM-PCR | | del 3 to 27 | 5 | 5 | 0 | 0 | 0 |
| QM-PCR | | del 18 to 27 | 3 | 2 | 1 | 0 | 1 |
| QM-PCR | | del P to 2 | 3 | 1 | 2 | 0 | 2 |
| QM-PCR | exon 17 | del 17 | 3 | 0 | 3 | 0 | 3 |
| QM-PCR | exon 13 | del 13 | 2 | 0 | 2 | 0 | 2 |
| Total mutations that occurred more than once | | | 199 | 97 | 102 | 14 | 88 |
| % of mutant alleles | | | | 50% | 56% | 45% | |
| Number of mutations that occurred only once | | | 202 | 75 | 127 | | |
| % of mutant alleles | | | | 50% | 44% | 55% | |
| Total number of mutant alleles excluding LOH | | | 401 | 172 | 229 | | |

Of 401 (229 germline, 172 somatic) RB1 mutations, 50% were unique and occurred only once (202 overall, 127 germline, 75 somatic) (Table 3). One third of the "recurrent" mutations were large deletions and methylation of the promoter and were not defined at a nucleotide level. All of the 13 point mutations that occurred four or more times involved C→T transitions at CpG dinucleotides attributed to deamination of 5-methylcytosine (Rideout et al. 1990; Schmutte and Jones 1998). Twelve of these mutations affected arginine codons and one created a splice mutation (1354+1 G→A).

Molecular analysis of tumor in one unilateral patient identified three individual RB1 mutations: heterozygous deletion of all exons and the promoter and S795X and 713delAA, both presumed to be hemizygous (rather than homozygous). Since tumors are clonal, it is possible that the three mutations represent two different subclones with different M2 mutations but with the same M1 deletion. None of the three mutations was present in the patient's blood. This is the only retinoblastoma tumor in which more than two RB1 mutations were observed, although mutation analysis of tumor DNA is discontinued once two genetic changes predicted to be causative have been identified.

Genotype-Phenotype Correlations

For 93% (186/199) of probands with bilateral retinoblastoma, the germline RB1 mutant alleles were "null" (Table 1) and were expected to result in premature truncation of translation and unstable mRNA [Dunn, 1989] due to nonsense-mediated decay [Hentze, 1999; Frischmeyer, 1999; Culbertson, 1999] resulting in no detectable protein. Of the 203 probands with null germline mutations, 92% had bilateral tumors, while only 50% (12/24) of probands with in-frame mutations developed bilateral tumors (Table 2). The diseased eye ratio (der) [Lohmann, 1994] (ratio of the sum of affected eyes to the number of mutation carriers in a family) is 1.9 for null RB1 alleles and <1.5 for in-frame and promoter mutant alleles.

The recurrent missense mutation R661W occurred in 7/229 unrelated families. Four of the seven R661W probands were unilaterally affected (der 1.6). Of 30 unilateral germline probands, four (13%) had R661W. This mutation has been associated with reduced penetrance [Lohmann, 1992; Onadim, 1992] and the protein product of the R661W allele has been shown to have partial activity [Otterson, 1997; Whitaker, 1998]. The sporadic unilateral patients with R661W germline mutations can therefore be considered the founders of reduced penetrance families. All of the 16 missense mutations involved the A/B "pocket" domain of pRB (FIG. 1), which is critical in the interaction of pRB with the transcription factor E2F [DiCiommo, 2000]. For example, in vitro studies of R661W showed decreased binding to the transcription factor E2F1 but retained ability to undergo cyclin-mediated phosphorylation (Otterson et al., 1997).

Lysine substitution for valine (V654L) resulted in reduced penetrance with der of 0.5, but substitution of glutamic acid for valine at the same position has been shown to yield a more highly penetrant phenotype (Lohmann, personal communication). A V654L mutant allele was also heterozygous with the null allele R556X in a unilateral non-hereditary tumor, consistent with the concept that LOH for the reduced penetrance V654L allele might be insufficient for tumorigenesis [DiCiommo, 2000]. Functional studies may provide greater insight into the importance of this valine residue, which lies 90-100% buried (Lee et al., 1998) within the pocket domain.

Of fifteen probands with complete deletion of RB1 (del P→27), only 11 (73%) had bilateral retinoblastoma. The del P→27 mutation accounted for 13% (4/30) of total unilateral germline mutations, but only 6% of all bilateral germline mutations (Table 1). The tendency for total deletions to cause fewer tumors has been hypothesized to be due to contiguous deletion of an adjacent unknown gene that is essential for cell survival [DiCiommo, 2000]. LOH for such a deleted allele, which is the M2 event in 52% of all tumors, would result inloss of the essential gene and cell death rather than retinoblastoma, resulting in a higher frequency of unilateral disease. Tumors would result only if M2 were a different mutation within RB1, leaving the "lethal" gene intact.

Sensitivity to Identify RB1 Mutation(s) in Probands some exons than for others (Table 4). For 19 exons, QM-PCR distinguished correctly between samples that have one allele and samples that have two alleles, at a 97% confidence level. For 22 exons, QM-PCR distinguished correctly at a 95% confidence level. For four exons, QM-PCR showed moderate power (confidence between 60% and 80%), and did not distinguish one from two copies of exon 1. We have developed a replacement set of four QM-PCR multiplex sets (Q1 to Q4) with between 1 and 13 exons each in order to increase overall effectiveness of mutation identification.

TABLE 4

Statistical ower of test for allelic uantity by QM-PCR.

| | Two-Copy | | Critical Value, | Implied | Implied Statistical Power (p = frequency NOT two-copy) | | |
|---|---|---|---|---|---|---|---|
| Exon | Sample Size (n) | Smallest α for zero β | measured as copy number | Confidence Level | Strong p > 0.95 | Moderate 0.60 < p < 0.95 | Weak 0 < p < 0.60 |
| 7 | 78 | 0% | 1.2 | 100% | X | | |
| 19 | 78 | 0% | 1.2 | 100% | X | | |
| 27 | 72 | 0% | 1.2 | 100% | X | | |
| 3 | 72 | 0% | 1.3 | 100% | X | | |
| 12 | 80 | 0% | 1.4 | 100% | X | | |
| 15/16 | 80 | 0% | 1.4 | 100% | X | | |
| 25 | 78 | 0% | 1.4 | 100% | X | | |
| 9 | 72 | 0% | 1.5 | 100% | X | | |
| 5 | 78 | 2% | 1.2 | 98% | X | | |
| 8 | 78 | 2% | 1.2 | 98% | X | | |
| 10 | 78 | 2% | 1.2 | 98% | X | | |
| 24 | 72 | 2% | 1.2 | 98% | X | | |
| 26 | 72 | 2% | 1.2 | 98% | X | | |
| 23 | 67 | 2% | 1.3 | 98% | X | | |
| 17 | 80 | 2% | 1.5 | 98% | X | | |
| 4 | 78 | 3% | 1.1 | 97% | X | | |
| 22 | 72 | 3% | 1.3 | 97% | X | | |
| 6 | 72 | 3% | 1.4 | 97% | X | | |
| 20 | 70 | 3% | 1.5 | 97% | X | | |
| 11 | 78 | 4% | 1.3 | 96% | X | | |
| 13 | 70 | 5% | 1.2 | 95% | X | | |
| 14 | 72 | 5% | 1.3 | 95% | X | | |
| 2 | 48 | 23% | 1.7 | 77% | | X | |
| 21 | 79 | 23% | 1.7 | 77% | | X | |
| 18 | 80 | 34% | 1.8 | 66% | | X | |
| P | 63 | 38% | 1.9 | 62% | | X | |
| 1 | 65 | 94% | 2.3 | 6% | | | X |
| | | | | CountTotals: | 22 | 4 | 1 |

In total, the combination of molecular techniques described above characterized 452 mutant RB1 alleles (Table 1). We identified the germline mutation in 199 of 224 bilateral probands (89% sensitivity) and in 17 of 20 (85%) unilateral familial probands. In the tumors from 134 unilateral sporadic patients we characterized 236 mutated alleles (89% sensitivity to discover mutant alleles). The germline status in 112 (84%) of these 134 patients was determined. No mutations were detected in the tumors of 8 unilateral sporadic probands. In tumors of 14 unilateral sporadic probands we characterized only one mutant allele that was not detected in blood. These 22 cases are considered incomplete. Thirteen (12%) of the 112 unilateral, sporadic probands had germline mutations despite the absence of family history.

QM-PCR Analysis

QM-PCR is sensitive to insertions and deletions ranging in size from one base (FIG. 4) to the whole RB1 gene. QM-PCR covering the whole gene in 6 multiplex sets of 1 to 8 exons (2, 1, 8, 6, 6 and 5 exons in six multiplex groups respectively) detected 31% of the mutant alleles in the sample. However, QM-PCR is a more powerful assay of allelic copy number for Alpha Risk: The probability of falsely categorizing two-copy DNA as one-copy DNA is α.

Beta Risk: The probability of falsely categorizing one-copy DNA as two-copy DNA is β.

Allele-Specific PCR

Analysis of mutation type and distribution along the RB1 gene revealed that although the gene lacks hotspots that would predict important functional domains, 13 point mutations recurred with significant frequency; CpG-transitions in particular (Table 3). AS4-PCR was developed for four of these recurrent mutations in one multiplex, which clearly distinguished the specific alleles from the background level of wild type allele amplification (FIG. 5). This multiplex is fast and inexpensive since only one PCR reaction and one agarose gel are required to detect 40/401 (10%) of all mutant alleles (12% of somatic and 8% of germline mutant alleles).

The instant invention reveals the importance of inter-dependencies between assays in at least two ways. First, characterization of some multi-exon deletions requires more than one multiplex. The sensitivity of the next multiplex therefore depends on the subset of multiplexes already performed. For example, multiplex Q2 scores 10, 13 or 17 mutations, depending on which multiplexes precede it in the test order. Consequently, QM-PCR multiplexes cannot be optimally ordered by a simple ratio of sensitivity over cost.

Isolating the set of QM-PCR multiplex permutations that achieve minimum time to discovery solves this problem. Materials cost and time differences were ignored, because each multiplex takes almost the same time and incurs almost the same materials cost. By scoring complete diagnosis and not partial deletions, it was found that, for bilateral probands, the unique best ranking of the revised Q1-4 multiplexes is 1-3-2-4 and for unilateral probands, 3-2-1-4. After the QM-PCR multiplexes were ordered, ranking of the entire list of tests proceeded with the added restriction that QM-PCR multiplexes maintain the optimal order.

Second, statistical dependence appears when analyzing sporadic unilateral mutations. In the 48% of tumors that do not show LOH, two different mutations must be searched. Any pair of mutations that occurs together with more than random probability introduces another source of history-dependent sensitivity ranking. The likelihood that the next assay will complete the molecular characterization of disease depends on which tests have already been performed. For example, it appears that methylation of the promoter is more likely (89%) than other kinds of mutations (48%) to be associated with LOH (Table 2). Using the method described above solved this problem.

For families with reduced numbers of affected eyes and frequent unilaterally affected children, the order of assays can be further optimized to reflect certain genotype/phenotype correlations. For example, in reduced penetrance families, 13% carry the R661W mutation. QM-PCR revealed the mutation in 40% of these patients, compared to 1% R661W and 32% QM-PCR-detectable mutant alleles for bilateral, full penetrance/expressivity families. Two families in the study showed the 745+1G→T mutation (IVS6+1G→T) and the characteristic inheritance pattern shown by Klutz et al. When paternally inherited, this splice mutation shows high expressivity and the nonsense-mediated decay of one copy of the mRNA as observed for other null RB1 alleles. Conversely, maternal inheritance of the mutation is associated with extremely low expressivity and the mis-spliced message is easily detectable [Klutz, 2002].

Impact of RB1 Mutation Identification on Quality of Health

Molecular analysis was useful to retinoblastoma families in several ways. A total of 12 of 30 offspring of adult retinoblastoma survivors who were tested at various stages of pregnancy or post-natally were shown to carry the family's mutation and all developed bilateral retinoblastoma. The offspring who did not carry the RB1 mutation did not develop retinoblastoma. Prenatal testing identified 9 fetuses that carried the family's RB1 mutation. Four of these pregnancies were terminated, all in families who had experienced children dying of retinoblastoma or second primary tumors. One family that had undergone a very negative experience with retinoblastoma terminated a pregnancy that carried the RB1 mutation and subsequently delivered a baby without the mutation, who did not develop tumors. Three families chose clinical examination as soon as the child was born which permitted early treatment of bilateral retinoblastoma tumors. Two of these three infants had bilateral tumors detected at birth. All three ultimately required enucleation of one eye when multiple treatments failed to control tumor growth.

Four infants were delivered prematurely around 35 weeks gestation in order to treat potential macular tumors early. One of the four infants had unilateral macular tumors at 36 weeks gestation. The other three children developed bilateral tumors one month to one year later. All 8 eyes were treated with laser and cryotherapy and all have 6/6 vision.

Only 13 of 113 (12%) of unilaterally affected probands with no family history of retinoblastoma were germline carriers of one of the two RB1 mutations detected in their tumor. None of the 100 unilateral probands whose identified tumor mutations where absent in blood developed retinoblastoma in the unaffected eye. Of all germline RB1 mutation carriers, approximately 10% [Sippel, 1998] are mosaic and might not be detected by our screens. A 1.2% (10%×12%) risk remains that a unilateral patient with no detectable mutation in blood has germline mosaicism with 0.6% residual risk for the next generation. Precise knowledge of the RB1 mutations in the tumor of a potentially mosaic unilateral proband permits accurate testing for those mutations in future offspring.

Infant relatives of retinoblastoma probands can be accurately tested. Within the cohort of 212 non-familial probands with germline mutations, >98% of parents tested normal for their child's mutation thereby predicting population risk for the development of retinal tumors in future children. Unidentified mosaicism however, puts siblings at a 0.5% (50% chance of inheriting mutant allele×10% chance the parent is an unaffected carrier×10% chance that the parent is mosaic) calculated risk of inheriting the same mutant RB1 allele as the proband. Since mosaicism cannot be inherited, the siblings and other relatives of unilateral retinoblastoma probands who do not manifest the mutations of the tumor in blood are at the population risk to develop retinoblastoma.

Impact of RB1 Mutation Identification on Cost of Health Care

To measure the impact of RB1 molecular testing on health outcomes and health care costs for whole families, we counted the number of surveillance examinations performed on first- and second-degree child relatives for a representative sample of 20 Ontario families (FIG. 6). For each family, we counted the number of examinations saved and the net savings in direct surveillance cost by the molecular strategy.

With molecular testing, individual relatives required fewer or no examinations for clinical surveillance. In the 20 families, 88 children avoided a total of 313 examinations under anaesthetic and 107 children avoided 852 clinic examinations (FIG. 6A). The mean savings in health care spending for all 20 families was CAD 6,591 (USD 4,200) per family (FIG. 6B). In 12 of 20 families surveyed, molecular analysis saved between CAD 1,000 and 38,000. In the remaining 8 families, surveillance with molecular analysis cost between CAD 1,000 and CAD 6,300 more than conventional surveillance. Even when the molecular strategy cost more, the quality of care was better for families in which molecular diagnosis allowed children to avoid clinical examinations. In five families, children at risk were relatively few or relatively old, so the usual savings were diminished. In one family that carries a low-penetrance mutation, a large proportion of people in the pedigree needed to be tested. In two families whose mutant RB1 allele was not identified by all the assays performed, the molecular route cost more because no clinical advantage was obtained despite the work.

Patient Samples

We examined 134 unilateral, non-familial probands and 224 bilateral or familial unilateral probands, referred from Canada, the United States and several other countries. All participating families provided informed consent for the research team to perform clinical tests and to use the samples for retinoblastoma research in an anonymous manner. No person selected the option to exclude their sample or information from research, in which case their information would have been excluded from this analysis.

Peripheral blood lymphocytes (PBL) of bilateral and familial unilateral patients were studied for RB1 mutations. Since few (15%) of the persons with sporadic unilateral retinoblastoma are predicted to have a germline RB1 mutation, failure to find a mutation in PBL is of marginal predictive value. Therefore, we searched unilateral tumor DNA for biallelic inactivating mutations and then examined PBL for those specific mutant alleles to rule in or out a germline mutation.

Total genomic DNA from PBL and tumor samples was extracted using the Puregene kit according to the manufacturer's directions (Gentra, Minneapolis, Minn.).

The sensitivity of the current invention was determined using a combination of QM-PCR, double-exon sequencing and methylation-specific PCR was calculated from the studied clinical samples. The sensitivity of allele-specific PCR was estimated by the ability to correctly identify four different mutations in control samples with previously identified mutations characterized by sequencing. For each assay, the cost (supplies and labor) and time to perform the assay was measured and the theoretical impact on overall test efficiency was calculated. The current invention was used to optimize the order of performance of the specific assays, based on the probability of revealing a mutation. The test turnaround time was calculated by defining the path that minimized time to mutation detection added to fixed handling time.

Molecular Techniques

Quantitative Multiplex PCR (QM-PCR)

QM-PCR was used to screen for changes in exon size and copy number. All 27 exons of the gene were amplified using intronic primers designed to include splice sites. The 3' end of the promoter, containing binding sites for ATF, E2F, SP1, AP1 and HRE elements [Gill, 1994], was amplified as a single fragment. Amplification was performed in six multiplex sets containing between 1 and 8 fluorescent-labelled primer pairs (Cy 5.5) that yielded products of different sizes to allow simultaneous visualization of fragments. Reactions were performed with AmpliTaq DNA Polymerase kit (Applied Biosystems, Foster City, Calif.). PCR conditions were optimized so that each exon was amplified quantitatively. Either a 282 by or a 329 by product from exon 4 of the human retinaldehyde binding protein gene (chromosome 15) was used as internal control for quantitation against external controls known to have the following RB1 status: nullisomic, WERI-RB1 retinoblastoma cell line [McFall, 1977]; monosomic, EL cell line [Benedict, 1983]; and diploid, normal. Amplified products were heat denatured, separated on a 6% polyacrylamide gel and analyzed using the OpenGene® Automated DNA System (Visible Genetics Inc, Toronto). Fragment detection and subsequent calculations were performed by the Gene Objects 3.1 software (Visible Genetics Inc, Toronto). Ratios of RB1 derived peaks to internal control peaks were used to calculate gene copy number. Size standards labelled with Cy5.5 were used to identify aberrantly migrating bands indicating suspect intra-exonic insertion or deletion, which were verified and further characterized by bi-directional sequencing.

When QM-PCR indicated suspect insertion or deletion involving one or more exons, long PCR was used to distinguish between true genetic alteration and artifacts generated by inefficient amplification due to intronic primer site polymorphisms. Amplimers were generated from genomic DNA using primers flanking the span of exons suspected to be deleted using the XL PCR kit according to the manufacturer's instructions (Perkin-Elmer). PCR products were analyzed by conventional agarose gel electrophoresis.

Accuracy of QM-PCR was analyzed by measuring the ability to distinguish one-copy from two-copy genotypes. Confidence limits for copy number were calculated under the assumption of binomial distributions of 195 observed independent trials.

Sequencing

Duplex PCR reactions that amplify pairs of exons were performed with AmpliTaq DNA Polymerase kit (Applied Biosystems, Foster City, Calif.). Each pair of exons was sequenced simultaneously using the Cy5/Cy5.5 Dye Primer Cycle Sequencing Kit (Amersham, Quebec/Visible Genetics Inc, Toronto). Each primer mixture contained two primers, each labelled with either Cy5 or Cy5.5, targeting exons amplified in the preceding duplex PCR. Primers were designed to include on average 50 base pairs of intronic sequence and therefore included traditionally recognized splice sites. Exons were duplexed based on similar mutation yields (to load early tests with positive results) or compatible reaction conditions. To sequence all 27 RB1 exons and promoter region, a total of 14 duplex sequencing reactions were performed. Sequences were analyzed and compared to wild type RB1 (Genebank Accession L11910) using the Open-Gene® Automated DNA System and Gene Librarian Software, Version 3.1 (Visible Genetics Inc., Toronto) to detect sequence alterations.

In naming mutations, the goal was to use a system that would most clearly identify the predicted result on the expected protein product. Conventional nomenclature as outlined by several authors (den Dunnen 2001) was used in naming mutations. Nucleotide position was numbered based on cDNA sequence, using the first base of the initiator codon as cDNA position number 1. Splice mutations were named according to their position relative to the closest exonic base where the first base 5' of the intronic-exonic boundary is denoted as −1 (and similarly +1 for the first base 3' of the intronic-exonic boundary). Mutations were also named by their effect on the amino acid at specific codons where relevant. RB1 mutations are also reported with reference to the genomic sequence accession No L11910 [Antonarakis, 1998].

Allele Specific-PCR (AS4-PCR)

PCR primers were designed for specific multiplex amplification of mutant sequences of four recurrent mutations, R358X, R251X, R579X and R455X in fragments of 202, 253, 287 and 730 bps respectively. The sense primers were specific for either the wild type or mutant genomic DNA templates at the ultimate 3' base position. Reactions were performed with AmpliTaq DNA Polymerase kit (Applied Biosystems, Foster City, Calif.). PCR conditions were optimized so that samples with these mutations would amplify strongly and only faint amplification would occur in the absence of the mutant alleles (for primer and template mismatches). Products were resolved by 2% agarose gel electrophoresis and the intensity of the amplified band indicated a mutant allele.

Promoter Methylation Assay

The degree of methylation in the RB1 promoter was determined by sodium bisulfite conversion and methylation-specific PCR (MS-PCR) as described in the literature [Zeschnigk, 1999] for tumor DNA of unilateral patients with no family history and with no or only one sporadic mutation revealed by QM-PCR and sequence analysis. PCR products from hypermethylated (201 bp) and normal (154 bp) RB1 promoter were separated on 2% agarose gel.

A variety of molecular techniques and assays may be employed for use with HOPE. These techniques and assays include, but are not limited to, quantitative multiplex PCR (QM-PCR), double-exon sequencing and promoter-targeted methylation-sensitive PCR.

The current invention, in its embodiments may be used for diagnosing mutations in DNA that relate to a variety of diseases, including, but not limited to breast cancer, colorectal cancer, lung cancer, prostate cancer, retinoblastoma and hereditary hemorrhagic telangiectasia.

It will be appreciated that the description above relates to the preferred embodiments by way of example only. Many variations on the system, method, and computer readable medium for delivering the invention will be understood to those knowledgeable in the field, and such variations are within the scope of the invention as described, whether or not expressly described.

REFERENCES

1. Antonarakis S E (1998) Recommendations for a nomenclature system for human gene mutations. Nomenclature Working Group. Hum Mutat 11:1-3
2. Benedict W F, Murphree A L, Banerjee A, Spina C A, Sparkes M C, Sparkes R S (1983) Patient with 13 chromosome deletion: evidence that the retinoblastoma gene is a recessive cancer gene. Science 219:973-5
3. Blanquet V, Turleau C, Gross-Morand M S, Senamaud-Beaufort C, Doz F, Besmond C (1995) Spectrum of germline mutations in the RB1 gene: A study of 232 patients with hereditary and non hereditary retinoblastoma. Hum. Mol. Genet. 4:383-388
4. Carter M S, Doskow J, Morris P, Li S, Nhim R P, Sandstedt S, Wilkinson M F (1995) A regulatory mechanism that detects premature nonsense codons in T-cell receptor transcripts in vivo is reversed by protein synthesis inhibitors in vitro. J Biol Chem 270:28995-9003
5. *Cystic Fibrosis Genotype-Phenotype Consortium* 1993. Correlation between Genotype and Phenotype in Patients with Cystic Fibrosis. N Eng J Med 329(18):1308-1313.
6. Den Dunnen J T, Antonarakis E (2001), Nomenclature for the description of human sequence variations Hum Genet 109:121-124
7. Den Dunnen J T, Grootscholten P M, Bakker E, Blonden L A, Ginjaar H B, Wapenaar M C, van Paassen H M, van Broeckhoven C, Pearson P L, van Ommen G J (1989) Topography of the Duchenne muscular dystrophy (DMD) gene: FIGE and cDNA analysis of 194 cases reveals 115 deletions and 13 duplications. Am J Hum Genet. 1989 December; 45(6):835-47
8. DiCiommo D, Gallie B L, Bremner R (2000) Retinoblastoma: the disease, gene and protein provide critical leads to understand cancer. Semin Cancer Biol 10:255-69
9. Dunn J M, Phillips R A, Zhu X, Becker A J, Gallie B L (1989b) Mutations in the RB1 gene and their effects on transcription. Mol. Cell. Biol. 9:4594-4602
10. Gad S, Aurias A, Puget N, Mairal A, Schurra C, Montagna M, Pages S, Caux V, Mazoyer S, Bensimon A, Stoppa-Lyonnet D (2001) Color bar coding the BRCA1 gene on combed DNA: a useful strategy for detecting large gene rearrangements. Genes Chromosomes Cancer. 2001 May; 31(1):75-84.
11. Hegde M R, Chong B, Fawkner M J, Leary J, Shelling A N, Culling B, Winship I, Love D R (2000) Hierarchical mutation screening protocol for the BRCA1 gene. Hum Mutat. 2000 November; 16(5):422-30.
12. Hentze M W, Kulozik A E (1999) A perfect message: RNA surveillance and nonsense-mediated decay. Cell 96:307-10
13. Janson M, Nordenskjold M (1994) A constitutional mutation within the retinoblastoma gene detected by PFGE. Clin Genet 45:5-10
14. Klutz M, Brockmann D, Lohmann D R (2002) A Parent-of-Origin Effect in Two Families with Retinoblastoma Is Associated with a Distinct Splice Mutation in the RB1 Gene. Am J Hum Genet 71:174-9
15. Lee J O, Russo A A, Pavletich N P (1998) Structure of the retinoblastoma tumour-suppressor pocket domain bound to a peptide from HPV E7. Nature 391(6670):859-65
16. Lohmann D, Horsthemke B, Gillessen K G, Stefani F H, Hofler H (1992) Detection of small RB1 gene deletions in retinoblastoma by multiplex PCR and high-resolution gel electrophoresis. Hum Genet 89:49-53
17. Lohmann D R, Brandt B, Hopping W, Passarge E, Horsthemke B (1994) Distinct RB1 gene mutations with low penetrance in hereditary retinoblastoma. Hum. Genet. 94:349-354
18. Lohmann D R (1999) RB1 gene mutations in retinoblastoma. Hum Mutat 14:283-288
19. McFall R C, Sery T W, Makadon M (1977) Characterization of a new continuous cell line derived from a human retinoblastoma. Cancer Res 37:1003-1010
20. Noorani H Z, Khan H N, Gallie B L, Detsky A S (1996) Cost comparison of molecular versus conventional screening of relatives at risk for retinoblastoma [see comments]. Am J Hum Genet 59:301-7
21. Otterson G A, Chen W, Coxon A B, Khleif S N, Kaye F J (1997) Incomplete penetrance of familial retinoblastoma linked to germ-line mutations that result in partial loss of RB function. Proc Natl Acad Sci USA 94:12036-40
22. Schmutte C, Jones P A (1998) Involvement of DNA methylation in human carcinogenesis. Biol Chem 379:377-88.
23. Sippel K C, Fraioli R E, Smith G D, Schalkoff M E, Sutherland J, Gallie B L, Dryja T P (1998) Frequency of somatic and germ-line mosaicism in retinoblastoma: implications for genetic counseling. Am J Hum Genet 62:610-9
24. Whitaker L L, Su H, Baskaran R, Knudsen E S, Wang J Y (1998) Growth suppression by an E2F-binding-defective retinoblastoma protein (RB): contribution from the RB C pocket. Mol Cell Biol 18:4032-42
25. Zeschnigk M, Lohmann D, Horsthemke B (1999) A PCR test for the detection of hypermethylated alleles at the retinoblastoma locus [letter]. J Med Genet 36:793-4

We claim:

1. A computer recordable medium having computer-executable instructions that when executed by a computer cause the computer to perform a method for determining an optimal genetic test order for diagnosing mutations that relate to a disease, the method comprising:
   a) generating a data set by:
      identifying known unique genetic mutations that relate to the disease and the frequency with which each mutation occurs in the population;
      identifying assays required to diagnose each of the mutations that relate to the disease;
      identifying the average cost of each assay; and
      for each assay, identifying the probability of a successful diagnosis of each of the mutations that relate to the disease;
   b) maintaining the data set to include new data received on the mutations that relate to the disease, the frequency distribution of mutations that relate to the disease and the assays required to diagnose the mutations that relate to the disease;

c) applying at least one decision tree algorithm, wherein the at least one decision tree algorithm comprises: (i) generating at least two strategies using the assays within the database; and (ii) ranking the at least two strategies by calculating the strategy expected cost for each of the at least two strategies;

d) identifying, from the ranked at least two strategies, the optimal genetic test order as the strategy with the lowest expected cost; and e) presenting the optimal genetic test order to a user via an output device.

2. The computer recordable medium of claim 1, wherein the strategy expected cost is calculated using the formula:

$$\text{Strategy Expected Cost} = \sum_{j=1}^{N} p_j \sum_{i=1}^{T_j} (C_{ij} - B_{ij})$$

where $C_{ij}$ is a cost of the i'th action performed along a j'th feasible search path; $B_{ij}$ is the value of all incremental benefits attained by the i'th action performed along the j'th feasible search path; $T_j$ is the total number of actions on search path j; N is the number of feasible search paths generated by a particular strategy; and $p_j$ is the likelihood that the search path j occurs and is approximated by the frequency distribution of empirically observed outcomes.

3. A system for determining an optimal genetic test order for diagnosing mutations that relate to a disease, comprising:

a) a computing environment;

b) an input device, connected to the computing environment for receiving data;

c) an output device, connected to the computing environment, for presenting data; and to a user; and d) an algorithm device for executing at least one decision tree algorithm based on at least a portion of the data received from the input device, wherein the at least one decision tree algorithm ranks at least a portion of the data and identifies the optimal genetic test order associated with the at least one decision tree algorithm, wherein the optimal genetic test order is the strategy with the lowest strategy expected cost and is presented to a user via the output device.

4. The system of claim 3, wherein the at least one decision tree algorithm further determines a projected cost for each genetic test associated with the optimal genetic test order, wherein the projected cost is presented to a user via the output device.

5. The system of claim 4, wherein the received data comprises the historical frequency distribution of mutations that relate to the disease and the assays required to diagnose the mutations that relate to the disease.

6. The system of claim 5, wherein the at least one decision tree algorithm is specific to hereditary diseases selected from the group consisting of breast cancer, colorectal cancer, lung cancer, prostate cancer, retinoblastoma, and hereditary hemorrhagic telangiectasia.

7. The system of claim 6, wherein the decision tree consists of at least two strategies.

8. The system of claim 7, wherein the at least two strategies are ranked by projected cost.

9. The system of claim 8, wherein the at least two strategies comprise at least two assays.

10. The system of claim 9, wherein the at least two strategies are ranked based on minimum projected cost to perform the at least two assays.

* * * * *